US011055565B2

(12) United States Patent
Boespflug et al.

(10) Patent No.: US 11,055,565 B2
(45) Date of Patent: Jul. 6, 2021

(54) SYSTEMS AND METHODS FOR THE IDENTIFICATION OF PERIVASCULAR SPACES IN MAGNETIC RESONANCE IMAGING (MRI)

(71) Applicant: Oregon Health & Science University, Portland, OR (US)

(72) Inventors: Erin L. Boespflug, Portland, OR (US); David Lahna, Portland, OR (US); Daniel Schwartz, Portland, OR (US); Lisa C Silbert, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 116 days.

(21) Appl. No.: 16/556,029

(22) Filed: Aug. 29, 2019

(65) Prior Publication Data
US 2020/0074214 A1     Mar. 5, 2020

Related U.S. Application Data

(60) Provisional application No. 62/724,568, filed on Aug. 29, 2018.

(51) Int. Cl.
*G06K 9/62* (2006.01)
*G06T 7/11* (2017.01)
(Continued)

(52) U.S. Cl.
CPC ............ *G06K 9/623* (2013.01); *A61B 5/0042* (2013.01); *A61B 5/055* (2013.01); *G06K 9/4638* (2013.01);
(Continued)

(58) Field of Classification Search
CPC .... G06K 9/623; G06K 9/4638; G06K 9/6288; G06K 9/4647; G06K 2209/05;
(Continued)

(56) References Cited

U.S. PATENT DOCUMENTS

| 6,430,430 B1 * | 8/2002 | Gosche | G06T 7/0012 |
| | | | 600/410 |
| 2014/0270052 A1 * | 9/2014 | Vestevich | A61B 6/501 |
| | | | 378/4 |

OTHER PUBLICATIONS

Ballerini, et al., "Application of the Ordered Logit Model to Optimising Frangi Filter Parameters for Segmentation of Perivascular Spaces," Procedia Computer Science, vol. 90, 2006, pp. 61-67.
(Continued)

*Primary Examiner* — Christopher M Brandt
(74) *Attorney, Agent, or Firm* — Lee & Hayes, P.C.; Katherine M. Mead; C. Rachal Winger

(57) ABSTRACT

Disclosed herein are methods and systems for the identification and characterization of perivascular spaces in the cerebral vasculature using magnetic resonance imaging (MRI) data. The disclosed methods allow for automated and unbiased quantification of enlarged perivascular space (ePVS) in a subject, and thus can provide a substantial improvement over manual grading methods used in the art. An example method includes receiving an MRI dataset including voxels having intensity values, identifying a set of candidate voxels within the MRI dataset based on the intensity values; grouping the set of candidate voxels into a set of first clusters; filtering the set of first clusters to generate a set of second clusters; and filtering the set of second clusters based on a morphologic constraint, thereby identifying an enlarged perivascular space in the MRI dataset.

20 Claims, 21 Drawing Sheets
(12 of 21 Drawing Sheet(s) Filed in Color)

(51) Int. Cl.
G06T 7/62 (2017.01)
G06T 7/13 (2017.01)
G06K 9/46 (2006.01)
A61B 5/055 (2006.01)
A61B 5/00 (2006.01)

(52) U.S. Cl.
CPC ......... *G06K 9/4647* (2013.01); *G06K 9/6288* (2013.01); *G06T 7/11* (2017.01); *G06T 7/13* (2017.01); *G06T 7/62* (2017.01); *G06K 2209/05* (2013.01); *G06T 2207/10076* (2013.01); *G06T 2207/10088* (2013.01); *G06T 2207/20036* (2013.01); *G06T 2207/30016* (2013.01); *G06T 2207/30101* (2013.01)

(58) Field of Classification Search
CPC .. G06K 9/342; G06T 7/11; G06T 7/62; G06T 7/13; G06T 2207/10076; G06T 2207/10088; G06T 2207/20036; G06T 2207/30016; G06T 2207/30101; A61B 5/055; A61B 5/0042
See application file for complete search history.

(56) References Cited

OTHER PUBLICATIONS

Bouvy, et al., "Perivascular spaces on 7 Tesla brain MRI are related to markers of small vessel disease but not to age or cardiovascular risk factors," J. Cereb. Blood Flow Metab., vol. 36, No. 10, 2016, pp. 1708-1717.

Bouvy, et al., "Visualization of Perivascular Spaces and Perforating Arteries With 7 T Magnetic Resonance Imaging," Invest. Radiol., vol. 49, No. 5, 2014, pp. 307-313.

Charidimou, et al., "White Matter Perivascular Spaces: An MRI Marker in Pathology-Proven Cerebral Amyloid Angiopathy?," Neurology, vol. 82, No. 1, 2014, pp. 57-62.

Chen, et al., "Assessment of the Virchow-Robin Spaces in Alzheimer disease, mild cognitive impairment, and normal aging, using high-field MR imaging," Am. J. Neuroradiol, vol. 32, No. 8, 2011, pp. 1490-1495.

Cox, "AFNI: Software for Analysis and Visualization of Functional Magnetic Resonance Neuroimages," Comput. Biomed. Res., vol. 29, No. 3, 1996, pp. 162-173.

Descombes, et al., "An Object-Based Approach for Detecting Small Brain Lesions: Application to Virchow-Robin Spaces," IEEE Trans. Med. Imaging., vol. 23, No. 2, 2004, pp. 246-255.

Eddins, "The Watershed Transform: Strategies for Image Segmentation," Technical Articles and Newsletter, 2002, 8 pages.

Gao, et al., "Complexity of MRI White Matter Hyperintensity Assessments in Relation to Cognition in Aging and Dementia From the Sunnybrook Dementia Study," J. Alzheimers Dis., vol. 26, No. 3, 2011, pp. 379-388.

Hernandez, et al., "Towards the Automatic Computational Assessment of Enlarged Perivascular Spaces on Brain Magnetic Resonance Images: A Systematic Review," Journal of Magnetic Resonance Imaging, vol. 38, No. 4, 2013, pp. 774-785.

Pantoni, et al., "Cerebral Small Vessel Disease: From Pathogenesis and Clinical Characteristics to Therapeutic Challenges," Lancet Neurol., vol. 9, No. 7, 2010, pp. 689-701.

Pieper, et al., "3D Slicer," IEEE International Symposium on Biomedical Imaging, 2004, 4 pages.

Pieper, et al., "The NA-MIC Kit: ITK, VTK, Pipelines, Grids and 3D Slicer as an Open Platform for the Medical Image Computing Community," 3rd IEEE International Symposium on Biomedical Imaging, 2006, 4 pages.

Potter, et al., "Cerebral Perivascular Spaces Visible on Magnetic Resonance Imaging: Development of a Qualitative Rating Scale and its Observer Reliability," Cerebrovasc. Dis., vol. 39, No. 3-4, 2015, pp. 224-231.

Promjunyakul, et al., "Characterizing the white matter hyperintensity penumbra with cerebral blood flow measures," Neuroimage Clin., vol. 8, 2015, pp. 224-229.

Ramirez, et al., "Visible Virchow-Robin Spaces on Magnetic Resonance Imaging of Alzheimer's Disease Patients and Normal Elderly from the Sunnybrook Dementia Study," J. Alzheimer's Dis., vol. 43, 2015, pp. 415-424.

Roher, et al., "Cortical and Leptomeningeal Cerebrovascular Amyloid and White Matter Pathology in Alzheimer's Disease," Mol. Med. vol. 9, No. 3-4, 2003, pp. 112-122.

Van den Heuvel, et al., "Measuring Longitudinal White Matter Changes: Comparison of a Visual Rating Scale with a Volumetric Measurement," Am. J. Neuroradiol., vol. 27. No. 4, 2006, pp. 875-878.

Wang, et al., "Development and initial evaluation of a semi-automatic approach to assess perivascular spaces on conventional magnetic resonance images," J. Neurosci. Methods, vol. 257, 2016, pp. 34-44.

Wardlaw, et al., "Neuroimaging Standards for Research Into Small Vessel Disease and Its Contribution to Ageing and Neurodegeneration," Lancet Neurol., vol. 12, No. 8, 2013, pp. 822-838.

Yakushiji, et al., "Topography and associations of perivascular spaces in healthy adults," Neurology, vol. 83, No. 23, 2014, pp. 2116-2123.

Zong, et al.. "Visualization of Perivascular Spaces in the Human Brain at 7T: Sequence Optimization and Morphology Charactenzation," Neuroimage, vol. 125, 2016, pp. 895-902.

\* cited by examiner

Table 1. Results

| | Visual single slice count correlations | Single slice repeated measurement correlations | Whole brain repeated measurement correlations | SNR$_{ePVS}$/ SNR$_{NAWM}$ | CNR(SD) |
|---|---|---|---|---|---|
| Visual | - | r$_{(12)}$=.86, p<.0001 | - | - | - |
| mMAPS | r$_{(26)}$=.73, p<.0001 | r$_{(12)}$=.52, p<.01 | r$_{(12)}$=.80, p<.001 | - | - |
| MAPS-T1 | r$_{(26)}$=.51, p<.01 | r$_{(12)}$=.96, p<.0001 | r$_{(12)}$=.97, p<.0001 | 36.2/48.8 | 12.6(2.7) |
| MAPS-T2 | r$_{(26)}$=.52, p<.01 | r$_{(12)}$=.91, p<.0001 | r$_{(12)}$=.81, p<.001 | 83.5/56.6 | 26.9(6.9) |

FIG. 11

SYSTEMS AND METHODS FOR THE IDENTIFICATION OF PERIVASCULAR SPACES IN MAGNETIC RESONANCE IMAGING (MRI)

CROSS-REFERENCE TO RELATED APPLICATION

The present patent application claims priority to U.S. Provisional Application No. 62/724,568, filed on Aug. 29, 2018, which is incorporated by reference herein in its entirety.

STATEMENT REGARDING FEDERALLY SPONSORED RESEARCH

This invention was made with government support under R01 AG036772 and P30 AG008017 awarded by the National Institutes of Health. The government has certain rights in the invention.

TECHNICAL FIELD

Generally, the field involves methods of image analysis and morphological characterization of features in MRI data sets. More specifically, the field involves automated methods of processing volumetric MRI scans to identify and measure perivascular space around the cerebral vasculature.

BACKGROUND

The term perivascular space (PVS), or Virchow-Robin space, refers to fluid-filled sheaths around the cerebral vasculature. This perivascular compartment serves as a conduit for waste elimination from the brain (DATA ACQUISITION AND PROCESSING BRAIN PATHOL, 2008. 18(2): p. 253-66; Abbott, N.J., NEUROCHEM INT, 2004. 45(4): p. 545-52; Iliff, J. J., et al., SCI TRANSL MED, 2012. 4(147): p. 147ra111). Enlarged perivascular spaces (ePVS), previously considered a normal neuroradiological variant (Groeschel, S., et al., NEURORADIOLOGY, 2006. 48(10): p. 745-54.), are increasingly considered a potentially clinically relevant finding because ePVS burden appears to be associated with clinical Alzheimer's disease (AD) status (Ramirez, J., et al., J ALZHEIMERS DIS, 2015. 43(2): p. 415-24), cerebral small vessel disease (Potter, G. M., et al., CEREBROVASC DIS, 2015. 39(3-4): p. 224-31; Patankar, T. F., et al., AJNR AM J NEURORADIOL, 2005. 26(6): p. 1512-20), cerebral amyloid angiopathy (CAA) (Charidimou, A., et al., NEUROLOGY, 2014. 82(1): p. 57-62), and multiple sclerosis (Wuerfel, J., et al., BRAIN, 2008. 131(Pt 9): p. 2332-40). Histopathological and magnetic resonance imaging (MRI) data indicate that ePVS are not simply a reflection of global atrophy; no association between brain weight (Roher, A. E., et al., MOL MED, 2003. 9(3-4): p. 112-22.) or brain parenchymal fraction (Wuerfel, J., et al., BRAIN, 2008. 131(Pt 9): p. 2332-40) was identified in previously reported clinical correlates of ePVS burden.

One important methodological consideration of identifying ePVS on MRI is the simultaneous interrogation of multiple sequences to differentiate ePVS from other lesions of vascular origin and to assess possible ePVS with respect to morphology, including linear shape and size (Wardlaw, J. M., et al., LANCET NEUROL, 2013. 12(8): p. 822-38). The ePVS are isointense to cerebrospinal fluid (CSF) on sequences; the most commonly used are T1- or T2-weighted (Id.). Although ePVS are commonly smaller than 3-5 mm in diameter, they can be as large as 10-20 mm (Id.; Hernández, M. D. C. V., et al., JOURNAL OF MAGNETIC RESONANCE IMAGING, 2013. 38(4): p. 774-785). The linear morphology of ePVS is an important feature in differentiating them from lacunar infarctions (Wardlaw, J. M., et al., LANCET NEUROL, 2013. 12(8): p. 822-38).

In vivo identification of ePVS on clinical MRI is well established using visual rating scales, which are based on relative signal intensity on T1-weighted MRI, T2-weighted MRI, or both (Potter, G. M., et al., CEREBROVASC DIS, 2015. 39(3-4): p. 224-31), with increased sensitivity from simultaneous consultation of multiple sequences, including fluid attenuated inversion recovery (FLAIR) (Id.) and proton density (PD) sequences (Pantoni, L., LANCET NEUROL, 2010. 9(7): p. 689-701). Visual rating scales, however, are limited in their sensitivity because they rely on subjective selection of the rating section, provide no information with respect to volume or morphology of ePVS, and may be unreliable across studies and laborious to implement. These limitations hinder research into the etiology and clinical relevance of ePVS. Specifically, categorical rating scales reduce the ability of investigators or clinicians to detect or track subtle longitudinal changes and are susceptible to the limitations of ceiling and floor effects (van den Heuvel, D. M., et al., AJNR AM J NEURORADIOL, 2006. 27(4): p. 875-8). In addition, previous studies at clinical field strengths have segmented only total ePVS volumes (Ramirez, J., et al., J ALZHEIMERS DIS, 2015. 43(2): p. 415-24), were limited to single-section assessment (Wang, X., et al., J NEUROSCI METHODS, 2016. 257: p. 34-44), required a substantial degree of subjective thresholding by the rater (Id.; Ballerini, L., et al., PROCEDIA COMPUTER SCIENCE, 2016: p. 61-67), or required high-spatial-resolution imaging not typically performed in clinical datasets (Bouvy, W. H., et al., INVEST RADIOL, 2014. 49(5): p. 307-13; Zong, X., et al., NEUROIMAGE, 2016. 125: p. 895-902; see also Descombes, X., et al., IEEE TRANS MED IMAGING, 2004. 23(2): p. 246-55). Thus there is a need for automated methods to assess counts and sizes of ePVS to reduce inconsistencies and disagreements between visual ratings approaches, increase statistical power to detect longitudinal changes, and operate on datasets obtained at clinical levels of spatial resolution.

SUMMARY

The present disclosure relates to methods and systems for the identification and quantification of enlarged perivascular spaces (ePVS) in the brain. Specifically, the disclosure relates to automated methods for segmentation and quantification of ePVS in magnetic resonance imaging (MRI) data. Various disclosed methods can be applicable to MRI data obtained using clinical-field-strength devices (for example, 3.0-T field strength MRI systems) as well as higher strength research-grade instruments. In addition, various techniques described herein can be applicable to normal (i.e., non-enlarged) PVS when image resolution is sufficiently high to distinguish such features.

In embodiments disclosed herein, methods are disclosed for analyzing MRI datasets to characterize various features of the voxels of the dataset and identifying groups of voxels that image ePVS in a subject. The methods can include a series of filtering steps or constraints to first identify a set of candidate voxels within the WM of a subject, and then can systematically reject subsets of those candidate voxels based on intensity, connectivity, and morphologic criteria to identify voxel clusters as ePVS. The disclosed methods are applicable to and may utilize a variety of different MRI sequence data for ePVS identification, including, but not limited to, T1w (T1-weighted), T2w (T2-weighted), FLAIR (fluid attenuated inversion recovery), and PD (proton density).

In some embodiments, the disclosed methods can include a set of steps to process MRI voxel image data as follows:

(1) Voxels within the WM mask are filtered based on local intensity variability within the normal appearing white matter to identify a set of candidate voxels that might be part of an ePVS.

(2) Candidate voxels are grouped into a set of clusters, each cluster in the set comprising voxels having contiguous connectivity; the set of clusters is filtered to identify a set of candidate clusters that might be an ePVS.

(3) Candidate clusters are filtered using morphological constraints that describe the linearity and the width of each candidate cluster to identify a final set of clusters to be classified as ePVS.

An aspect of the disclosed methods is that they allow for automated and unbiased quantification of enlarged perivascular space (ePVS) in a subject. Further, various disclosed methods may be applied to MRI data from successive imaging sessions to track changes in ePVS burden over time.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

BRIEF DESCRIPTION OF THE DRAWINGS

The detailed description is described with reference to the accompanying figures. This application contains at least one drawing executed in color. Copies of this application with color drawing(s) will be provided by the Office upon request and payment of the necessary fee.

FIG. 11: A table showing a comparison of the results obtained using visual rating, mMAPS, MAPS-T1, and MAPS-T2 approaches.

DETAILED DESCRIPTION

Figure 1:
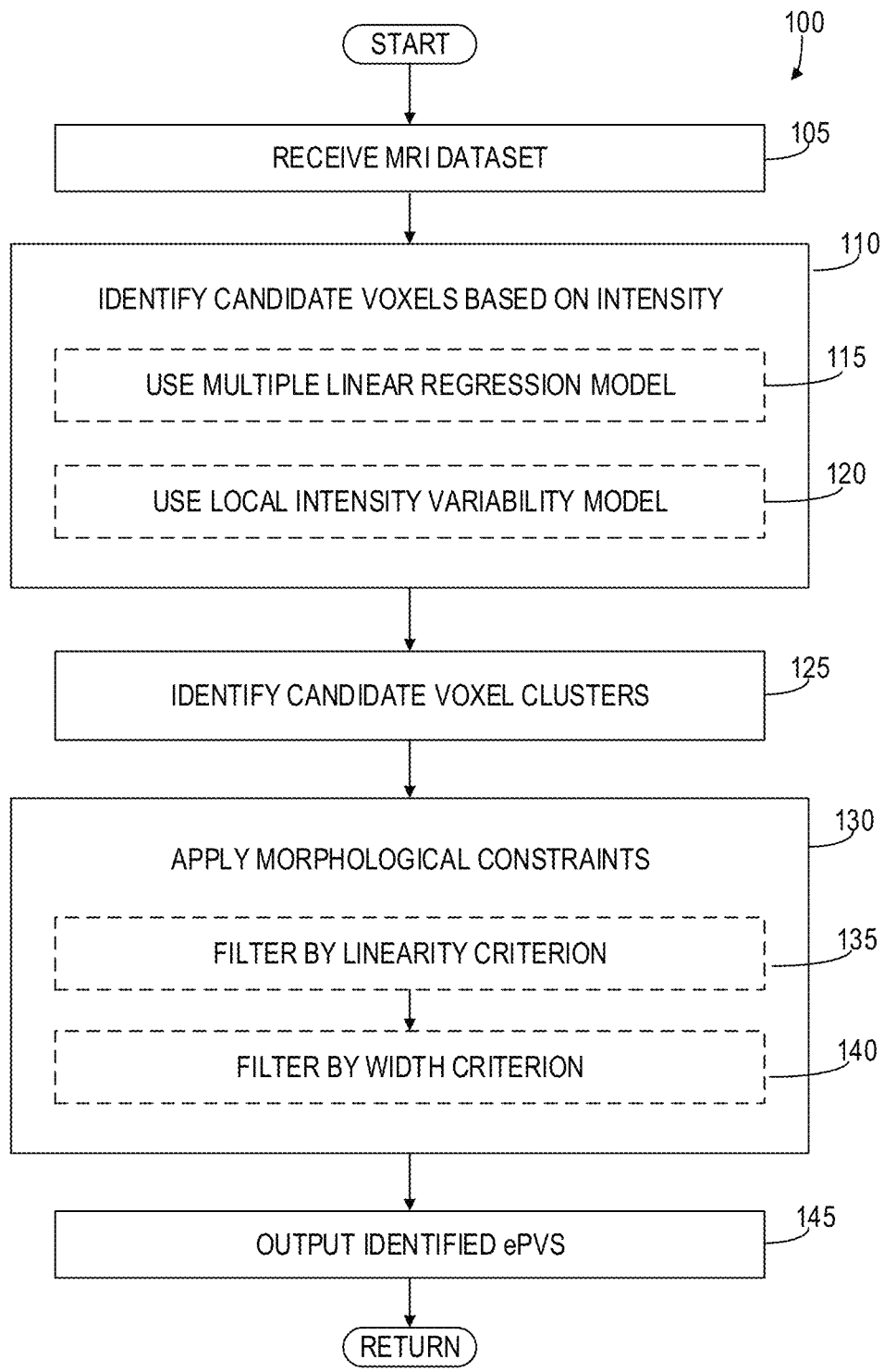
FIG. 1: An exemplary flowchart of steps performed to identify ePVS and/or PVS in a volumetric MRI dataset.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

Disclosed herein are systems and methods for identifying ePVS in MRI datasets. The disclosed methods are applicable to and may utilize a variety of different MRI sequence data, including, but not limited to, T1w (T1-weighted), T2w (T2-weighted), FLAIR (fluid attenuated inversion recovery), and PD (proton density). As used herein, an MRI dataset may comprise one or more different types of MRI sequence data obtained from a subject, wherein the different types of sequence data may be co-registered to anatomically align the data from different scan types.

The systems and methods described herein may also be used to identify normal PVS (i.e., not enlarged), provided that the voxel resolution of the MRI images is sufficient to discriminate such features. It is to be understood that where the terminology ePVS is used throughout this application, the same systems and methods may also be used to detect PVS when MRI datasets of sufficient resolution are available.

Perivascular spaces may be enlarged in healthy humans and not imply a disease state. In some embodiments, an enlarged periovascular space (ePVS) may be defined as a perivascular space of greater than 3 millimeters (mm) in diameter. In some embodiments, enlarged perivascular space may be defined as a perivascular space of greater than 4 mm in diameter. In other embodiments, an enlarged perivascular space may be one that is greater than 5 mm in diameter, greater than 6 mm in diameter, greater than 7 mm in diameter, greater than 8 mm in diameter, greater than 9 mm in diameter, greater than 10 mm in diameter, greater than 15 mm in diameter, or greater than 20 mm in diameter.

Conversely, a non-enlarged perivascular space may be one of equal to or less than 3 mm in diameter. In other embodiments, a non-enlarged perivascular space may be one that has a determined diameter of equal to or less than 4 mm, 5 mm, 6 mm, 7 mm, 8 mm, or 10 mm.

The disclosed methods are useful for analyzing newly acquired MRI datasets or for MRI data that have been previously acquired and stored for retrospective analysis. In addition, the disclosed methods may be used in longitudinal studies to track changes in ePVS burden over time in a subject.

In some embodiments, it may be necessary to perform preprocessing operations on MRI datasets that are to be interrogated for the presence of ePVS. For example, in some embodiments, bias field correction may be applied to volumetric MRI data. In addition, alignment of two or more MRI data sets may be performed using co-registration techniques known in the art. For example, when T1w, T2w, FLAIR, and PD volumes are acquired, one may register the T2w, FLAIR, and PD volumes to the T1w dataset using co-registration techniques known in the art.

As part of the methods disclosed herein, MRI datasets may be segmented into tissue types using methods known in the art to generate masks for different tissue types. Exemplary tissue types for which masks may be created include white matter (WM), cortical gray matter (GM), subcortical gray matter (BG), and ventricular CSF (vCSF). In some embodiments WM masks may be corrected for tissue misclassification due to white matter hyperintensities (WMH), wherein WMH are included in the final WM mask (see, for example, the method described in Promjunyakul, N., et al., NEUROIMAGE CLIN, 2015. 8: p. 224-9). In further embodiments, morphological operations such as erosion or dilation may be applied to masks as needed. For example, ventricular masks may be eroded by one or more voxels to mitigate partial volume effects at the ventricle anatomic boundary.

FIG. 1 shows an exemplary flowchart 100 depicting a set of steps for identifying ePVS in an MRI dataset of a subject. At 105 an MRI dataset is received. This MRI data set may comprise a plurality of different types of MRI sequence data (for example, T1, T2, FLAIR, and PD sequence data that has been co-registered and segmented to generate masks for different tissue types). At 110 an intensity modeling approach is used to identify candidate ePVS voxels within the WM masked region of the data sets. The intensity modeling approach used at 110 may be implemented in a number of ways and depends, in part, on the types and characteristics of the of MRI image sequences available in the MRI dataset. As one example, at 115 a multiple linear regression model is used to identify candidate. An exemplary multiple linear regression approach to identify candidate ePVS voxels is described in Example 1. An alternate approach for intensity modeling to identify candidate voxels, at 120, is to use a local intensity variability model to characterize intensity values in a neighborhood of voxels. In this approach voxels having intensity values that are "outliers" compared to the local neighborhood of voxels are identified as candidate voxels for further classification. Exemplary approaches for implementing a local intensity variability model are shown in Examples 2 and 3.

Candidate voxels identified by the intensity model at 110 are grouped into clusters at 125. The clusters defined in this step are comprised of a set of candidate voxels that are contiguously connected. In some embodiments, two voxels may be considered to be connected if they share a single common voxel vertex (i.e., they have "touching corners"). In alternate embodiments, two voxels may be considered connected if the share a common edge or a common face. Once the candidate voxels are grouped into a set of clusters, the clusters are filtered by size or volume. Clusters having a volume below a prescribed threshold (or, alternatively, clusters having fewer than a prescribed number of voxels) are identified and removed (i.e., the clusters are filtered by size), and the remaining candidate clusters are submitted to a morphological constraint model at 130.

In the morphological constraint model 130, each of the candidate clusters is characterized according to a metric of its spatial linearity 135 and a metric of its width 140.

In some embodiments, a linearity metric for a candidate cluster of voxels may be determined at 135 by fitting a line, for example, a best-fit line in the least squares sense, through the cluster of voxels in three-dimensional space. In another embodiment, the linearity of a given cluster may be characterized using singular value decomposition (SVD), wherein a vector associated with the largest eigenvalue of the decomposition is calculated. This vector denotes the principal axis about which voxels comprising a candidate clusters are positioned, for which the magnitude of the perpendicular vectors (norms) from each voxel in the cluster to said vector is minimized (i.e., an orthogonal regression). Candidate clusters having a linearity metric that lies within a prescribed range are further characterized by a width metric at 140. Methods for quantifying the width of irregularly shaped objects known in the art may be employed for this calculation. In some embodiments the line or vector fit through a given set of candidate cluster voxels at 135 may be used to determine a width metric for said cluster at 140, for example, by calculating perpendicular distance from the best fit line to cluster voxel vertices and defining a width metric therefrom. Candidate clusters having a width metric that exceeds a specified anatomic range for ePVS width are rejected from further consideration. The remaining candidate clusters having both linearity and width metrics that lie within a prescribed range of values are identified as ePVS the MRI dataset and results output at 145. These identified clusters may be used to quantify and report ePVS burden in the subject from whom the MRI dataset was obtained.

EXAMPLES

The following examples are illustrative of the disclosed methods. In light of this disclosure, those skilled in the art will recognize that variations of these examples and other examples of the disclosed method would be possible without undue experimentation.

Example 1—Application to Multiple Sequence Image Data

Abstract

A fully automated segmentation method that provides object-based morphology estimates of enlarged perivascular spaces (ePVS) in clinical field-strength (3 Tesla [T]) magnetic resonance imaging (MRI) data is reported.

Methods:

MRI data were obtained using a 3.0T Siemens Trio MRI from dementia-free research participants (mean age, 85 years, range=70-101 years) who had given written informed consent. This method is built on 1) relative normalized white matter (WM), ventricular and cortical (GM) signal intensities within T₁-weighted, fluid attenuated inversion recovery (FLAIR), $T_2$-weighted, and proton density (PD) data, and 2) morphological (width, volume, linearity) characterization of each resultant cluster. Visual rating was performed by three raters, including one neuroradiologist, following established single slice guidelines. Correlations between visual counts and automated counts, as well session-to-session correlation of counts within subject, were assessed by Pearson's r (Pearson correlation coefficient).

Results:

There was a significant correlation between counts by visual raters and automated detection of ePVS in the same slice (r=0.65, p<0.001; r=0.69, p<0.001; r=0.54, p<0.01). With regard to visual ratings and whole-brain count consistency, average visual rating scores were highly correlated with automated detection of total burden volume (r=0.58, p<0.01) and total ePVS number (r=0.76, p<0.01). Morphology of clusters across 28 datasets is consistent with published radiographic estimates of ePVS; mean width of clusters segmented was 3.12 mm (range: 1.7 mm to 13.5 mm).

Conclusion:

This MRI-based Multimodal Autoidentification of Perivascular Spaces (mMAPS) method provides individual whole brain morphological characterization of ePVS in clinical MRI data, and presents an important tool for detailed assessment of these features.

Methods

Neuroimaging data were acquired as part of ongoing research at the NIA-Layton Aging and Alzheimer's Disease Center at Oregon Health & Science University (OHSU) in Portland, Oreg., USA. The research protocol was approved by the OHSU Institutional Review Board, and all study participants considered in Example 1 signed informed consent documents prior to study enrolment and signed HIPAA authorization. Data were collected at two time points from 14 participants (demographics in Table 1). All participants studied in Example 1 were dementia-free older adults (mean age 85.3 years, range 70.4 to 101.2) living independently in the community. Presence or absence of lacunar infarction was not an exclusion criterion. Half (N=14) were used as the development dataset, and the other half (N=14) were used for testing the optimized model. Visit order (visit 1 or visit 2) was distributed evenly between development and test sets. For all datasets considered in Example 1, visual ratings were made by three independent raters, one of whom is board certified in neuroradiology (JP) with 10.5 years of experience, and two raters each with at least 10 years of MRI experience using an established visual rating scale (Potter, G. M., et al., CEREBROVASC DIS, 2015. 39(3-4): p. 224-31.). Briefly, each rater was given the published guide (Id.) and spatially co-registered $T_1$-weighted, $T_2$-weighted, and FLAIR images and was asked to select the axial slice through the centrum semiovale with the highest burden. On each rater's selected slice, they marked the location of each identified ePVS on the entire slice. Per the rating scale, categorical rating was assessed on a single hemisphere. However, the algorithm was developed to detect ePVS in the whole brain, and thus comparisons of mMAPS and visual ratings were also performed on actual counts on both hemispheres in a single slice.

TABLE 1

Participant Characteristics

| Characteristic | Finding |
|---|---|
| Age (y)* | 85.3 (70.4-101.2) |
| Sex (M/F) | 6/8 |
| Systolic blood pressure (mm Hg) | 129.9 ± 11.54 |
| Diastolic blood pressure (mm Hg) | 71 ± 7.60 |
| ICV (cm³) | 1871.59 ± 202.79 |
| WMH (cm³) | 12.32 ± 10.24 |
| MMSE score * | 28.36 (22-30) |
| CDR score (%)* | 83 (0.0-0.5) |
| CSO PVS Count* | |
| Rater 1 | 6.21 (1-14) |
| Rater 2 | 4.86 (1-14 |
| Rater 3 | 3.82 (1-13) |

Data Acquisition and Processing:

MRI data were obtained using a 3.0T Siemens Trio MRI (TIM Trio System, Siemens Healthineers, Erlangen, Germany). Three sequences were acquired: 3D T1-weighted magnetization prepared rapid gradient echo ([MPRAGE/T1]: TR/TE/TI/FA=2300 ms/3.41 ms/1200 ms/12°, 128 sagittal 1 mm slices with no gap, FOV=256×192 mm, imaging matrix=256×192, resulting in 1 mm isotropic voxels); 2D fluid attenuated inversion recovery ([FLAIR]: TR/TE/TI/FA=9000 ms/87 ms/2500 ms/100°, 95 axial 2 mm slices with no gap, FOV=228×248 mm, imaging matrix=236×256, resulting in in-plane resolution of 0.969×0.969 mm, 2 averages), and a 2D turbo spin echo-dual spin echo ([T2]/[PD]: TR/TE1/TE2/FA=3000 ms/11 ms/101 ms/150°, 48 axial 3 mm slices with no gap, FOV=240×214 mm, imaging matrix=256×228, resulting in an in-plane resolution of 0.938×0.938).

Figure 2:
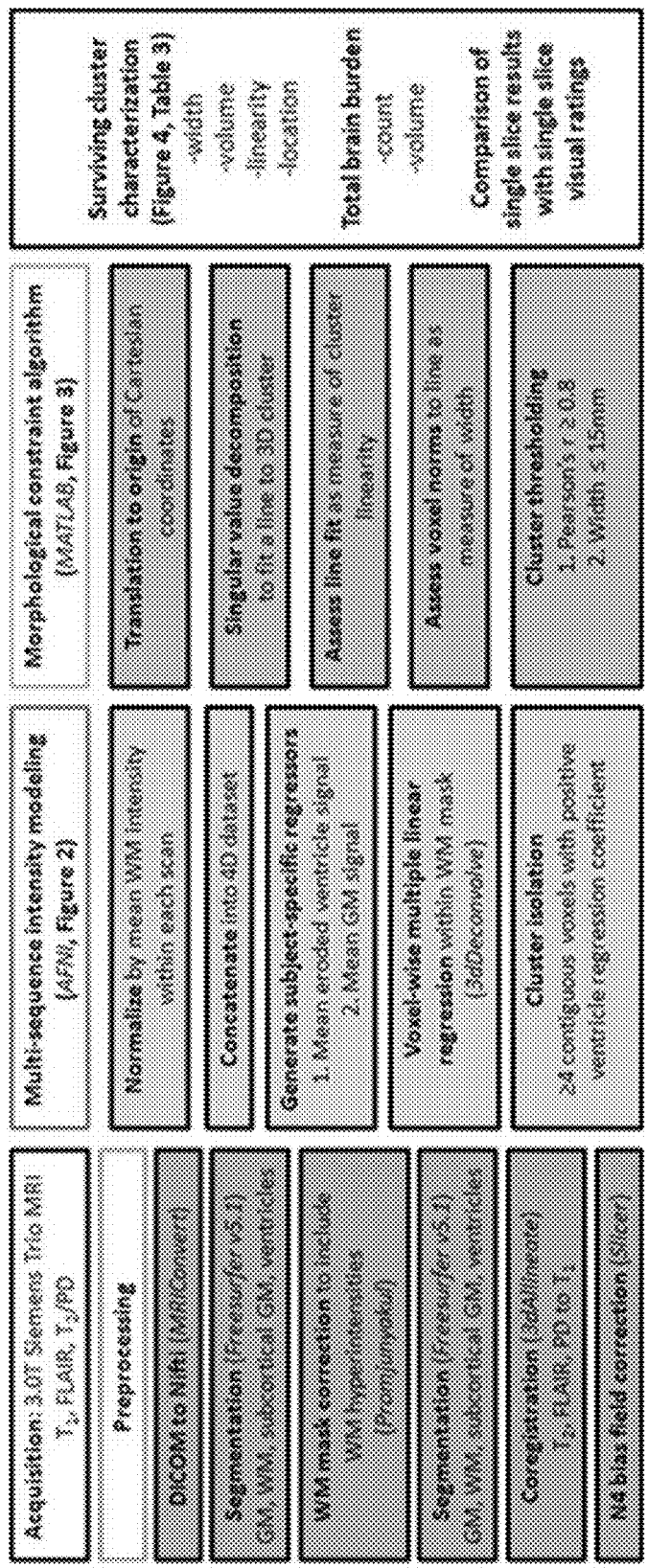
FIG. 2: Work flow diagram. AFNI=Analysis of Functional NeuroImages, DICOM=Digital Imaging and Communications in Medicine, GM=gray matter, PD=proton density, 3D=three-dimensional, 4D=four-dimensional, WM=white matter.

A full schematic of processing used in this Example 1 is shown in FIG. 2. Raw scanner DICOM files were converted to NIFTI (Neuroimaging Informatics Technology Intitiative) format using the publicly available software program MRI-Convert. T1-weighted images were bias field corrected and segmented into tissue types using Freesurfer v5.1, which yielded masks of white matter (WM), cortical gray matter (GM), subcortical gray matter (BG), and ventricular CSF. WM masks were corrected for tissue misclassification due to white matter hyperintensities (WMH), meaning that WMH were included in the final WM mask, by the method described in Promjunyakul, N., et al., NEUROIMAGE CLIN, 2015. 8: p. 224-9. Ventricular masks were eroded by a single voxel to avoid the potential of partial volume effects.

Figure 3A:
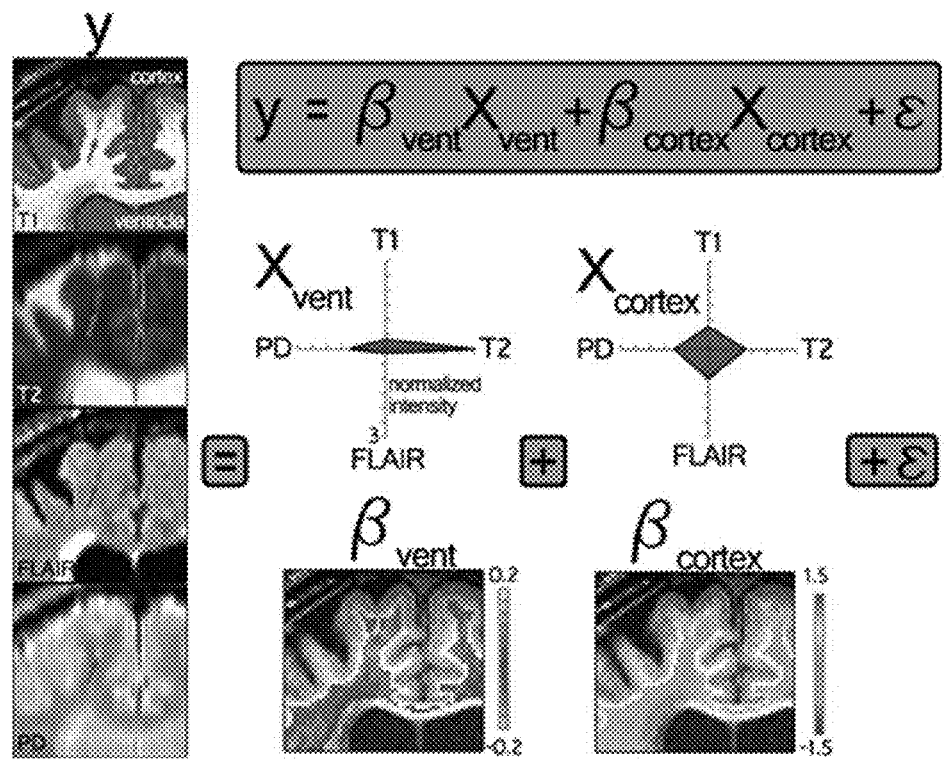
FIG. 3A: A graphical depiction of intensity-based voxel-of-interest detection with voxelwise regression run within white matter voxels. Radar plots represent one participant's CSF predictor (green, Xvent) and gray matter predictor (red, Xcortex). Bvent and Bcortex are regression coefficients associated with Xvent and Xcortex, respectively. PD=proton density.
Figure 3B:
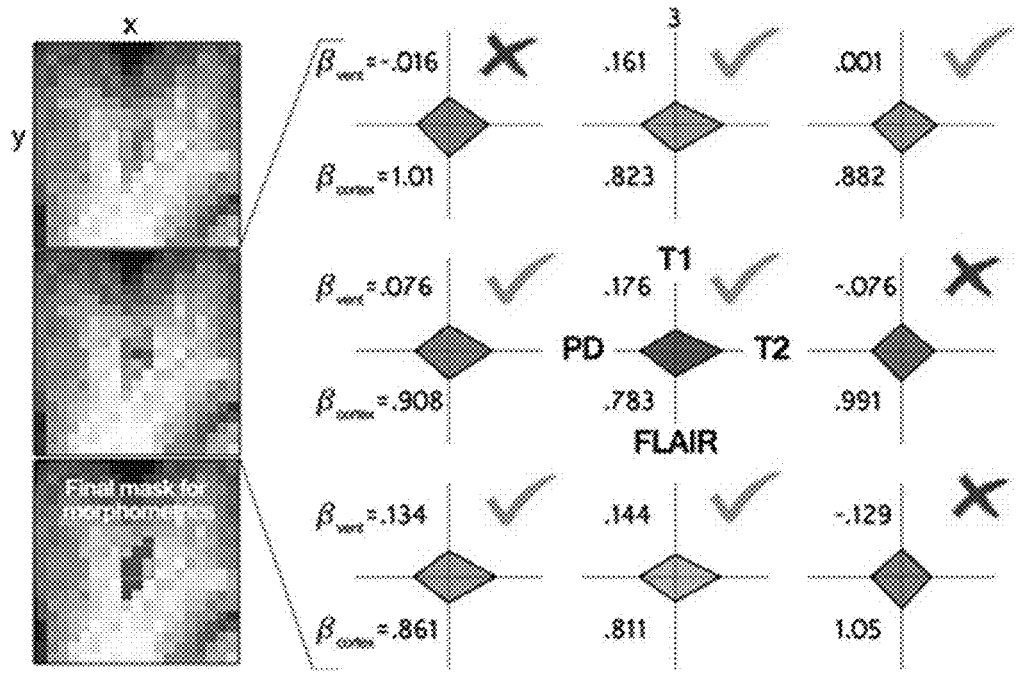
FIG. 3B: A graphical depiction of intensity-based voxel-of-interest detection where each radar plot depicts the fingerprint across sequences for that color-coded voxel shown on the left middle and derived regression coefficients for nine voxels centered on an identified PVS in a coronal section. Bvent and Bcortex are regression coefficients associated with Xvent and Xcortex, respectively. PD=proton density.

All four volumes (T1w, T2w, FLAIR, and PD) were corrected for B0 inhomogeneity using N4 bias field correction as implemented in Slicer3 (https://www.slicer.org; Pieper S., L. W. E., et al., THE NA-MIC KIT: ITK, VTK, PIPELINES, GRIDS AND 3D SLICER AS AN OPEN PLATFORM FOR THE MEDICAL IMAGE COMPUTING COMMUNITY. 2006. p. 698-701). For each subject's single time-point dataset, the homogenized T2w, FLAIR, and PD volumes were registered to the T1w dataset using 3dAllineate (Cox, R. W., AFNI, COMPUT BIOMED RES, 1996. 29(3): p. 162-73) with free shift and rotate parameters (6 degrees of freedom). The average intensity value of each sequence within the WM mask was used to normalize each sequence with respect to one another by dividing each voxel by that single value ("intensity normalization", 3dcalc), and the datasets were concatenated to create a single 4D dataset (3dTcat). Four element vectors were generated that described the average intensity of each volume in the ventricular mask and in the GM mask (3dmaskave), yielding two predictors for submission to voxel-wise multiple linear regression, which was performed within the WM mask (3dDeconvolve, FIG. 3A). A GM predictor was included as a nuisance predictor in order to account for variance associated with partial volume effects in and around ePVS, and to sensitize the ventricular (vCSF) predictor; the vCSF volume is largely free fluid signal, which is not well represented in ePVS for which fluid is constrained. This effect can be appreciated by comparing the Xvent predictor's T2-weighted signal with the voxels in the ePVS below it in FIG. 3A and FIG. 3B. Clusters (defined as voxels with "touching corners" and equal to or larger than 4 voxels) for which the ventricular predictor's regression coefficient was positive were retained (3dclust) for morphology-based evaluation.

Figure 4A:
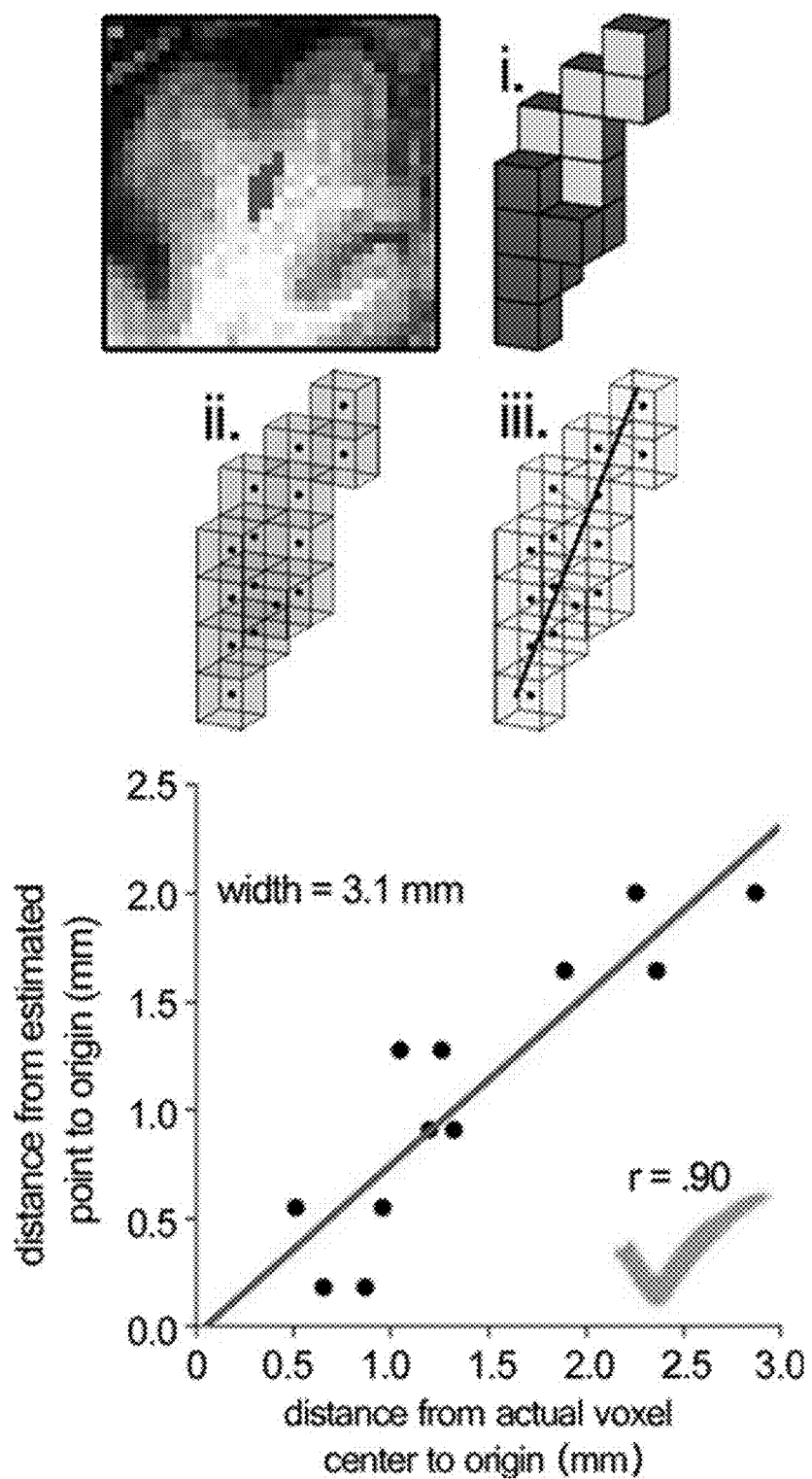
FIG. 4A: Morphologic testing example showing a preserved cluster after morphologic constraint. Yellow voxels (i) are marked in red in the section on the top left. The voxels are marked as points by their centers (ii), and norms are fit from each voxel to the line derived from singular value decomposition (red lines, iii). The correlation of distances to the center of each cluster from the voxel locations and the point on the line from each voxel's respective norm is the measure of linearity of a given cluster. The summed distance of the two farthest points from the line and 1.7 (the corner-to-corner distance of a 1-mm unit cube) are the width of the cluster.
Figure 4B:
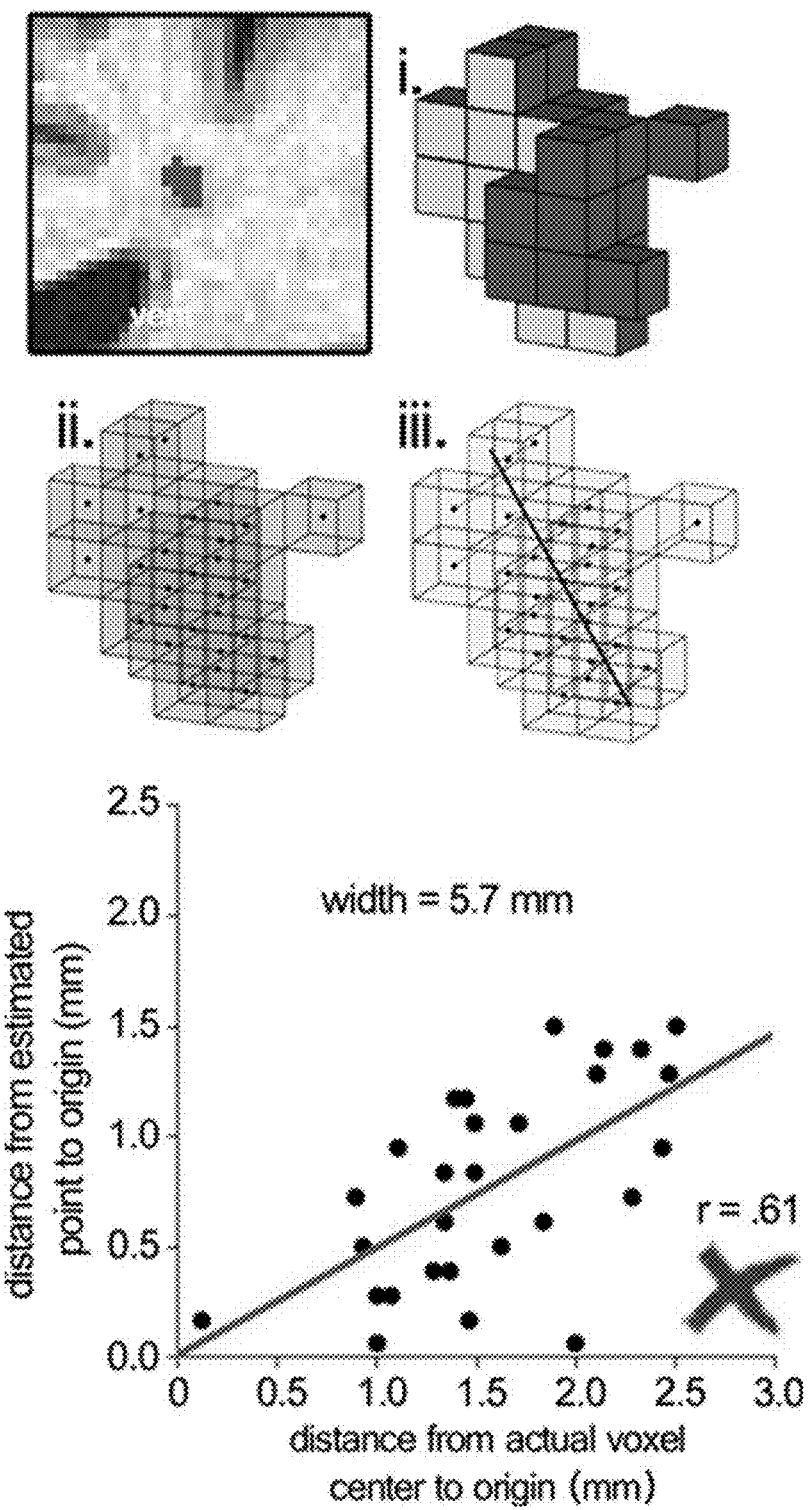
FIG. 4B: Morphologic testing example showing a cluster that was not preserved on the basis of low linearity (r<0.8), although the width of the cluster met the width constraint (<15 mm).

Surviving cluster coordinate sets were submitted to a morphological constraint algorithm (FIG. 4A and FIG. 4B), which was developed and executed in MATLAB 2014B (Mathworks, Natick, Mass.). Briefly, each coordinate set (X) was translated to the origin by subtracting the mean of each coordinate. Singular value decomposition was used to identify the vector (V1) associated with the largest eigenvalue, which was defined as the principal axis about which the cluster could be rotated and for which the magnitude of perpendicular vectors (norms) from each coordinate to V1 (Xerr) was minimized, as in orthogonal regression. The coordinate of V1 that lay on the same orthogonal plane at each coordinate of Xerr was defined as Xhat. For each coordinate in X and in Xhat the minimum Euclidean distance to the origin was calculated (Xdist and Xhatdist) and the two distance vectors were correlated using Pearson's correlation coefficient, r. Clusters that met the threshold of r>0.8 were considered to have met the linearity constraint. The sum of the largest norm and a norm whose vector had opposite direction in the same plane and 1.7 mm (the corner-to-corner distance of a mm unit cube) was taken as the width of the cluster; any cluster with a width smaller than 15 mm was considered to have met the width constraint. This maximum width threshold was selected based on the maximum diameter reported in the existing literature of 15 mm (see Hernández, M. D. C. V., et al., JOURNAL OF MAGNETIC RESONANCE IMAGING, 2013. 38(4): p. 774-785, for review). In this Example, all previously identified clusters that met both the linearity and width constraints were considered ePVS, the final mask containing the surviving clusters was printed to NIFTI format and summary statistics were carried out in AFNI and SPSS.

The total time to process and generate ePVS volume masks was approximately 1 hour for a single participant, and required approximately 1-2 minutes of human interaction (for quality assurance of the tissue segmentations and co-registrations). The pipeline was fully scripted and highly reproducible given the presence of necessary publicly available software as listed. The three visual raters reported approximate per-subject single slice rating times of 3-6, 5, and 6 minutes, respectively, which corresponded to a minimum time for a whole brain expert rating of approximately 5 hours (there were approximately 100 axial slices in white matter in the brain, at 3 minutes each).

WM and PVS signal-to-noise ratios (SNR) before and after intensity normalization in each sequence were calculated by dividing the mean intensity in the subset of WM voxels that were not identified as ePVS or in the mMAPS PVS mask by the standard deviation of an extracranial noise region-of-interest. Similarly, PVS contrast-to-noise ratio (CNR) was calculated by dividing the absolute value of the difference of the subset of WM voxels that were not identified as ePVS and PVS by the standard deviation of noise.

Comparisons of the visually identified ePVS on a single slice were performed by counting the number of ePVS identified by the algorithm in the same slice that was identified by each rater. In some cases, raters chose a different axial slice as the slice "with the highest burden" to rate; therefore, visually identified burden was calculated as the mean count of ePVS over all three raters utilized by Example 1 in each dataset (FIG. 5C).

An ePVS spatial probability map was calculated for visualization of the spatial distribution of mMAPS-identified ePVS in all datasets considered in Example 1. Briefly, all final ePVS masks considered in Example 1 were summed over all subjects considered in Example 1 (3dTcat, 3dTstat), blurred with a 3 mm FWHM 3d Gaussian kernel (3dmerge), overlaid on a representative T1-weighted image, and masked by the eroded ventricle mask and cortical mask (FIG. 5F). The highest frequency of identified ePVS in a single voxel was 3 out of 28 datasets (11%).

Results

Figure 5A:
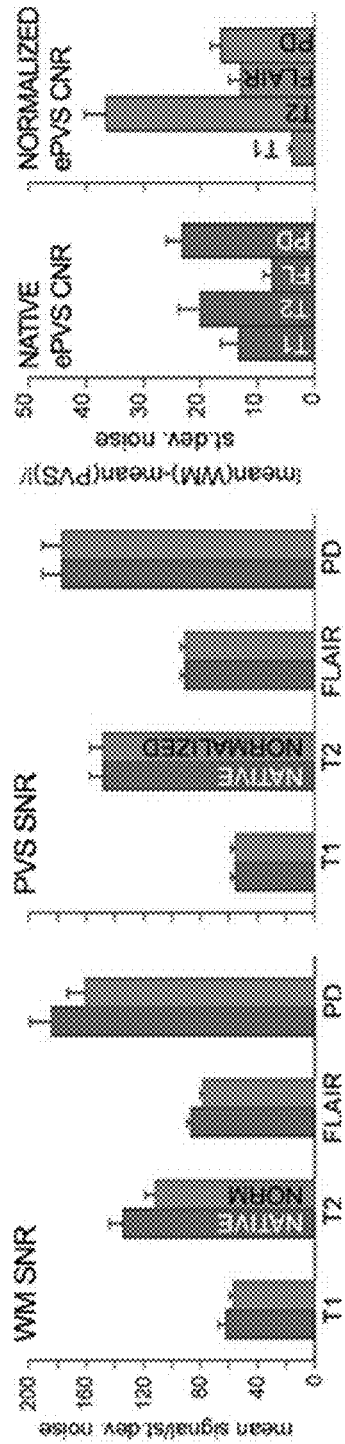
FIG. 5A: Signal-to-noise ratio (SNR) for normal-appearing white matter versus ePVS and contrast-to-noise (CNR) for native versus normalized ePVS. PD=proton density, WM=white matter.

The subset of WM not identified as ePVS and ePVS SNR and CNR for each sequence before and after intensity normalization are shown in FIG. 5A, with standard error of the mean (SEM) error bars. Intensity normalization decreased T1 ePVS CNR (paired t=3.00, p<0.01), increased T2 ePVS CNR (paired t=−4.28, p<0.001), increased FLAIR ePVS CNR (paired t=−4.31, p<0.001), decreased PD ePVS CNR (paired t=2.27, p<0.04) and reduced CNR SEM of T1-weighted and PD datasets.

Figure 5B:
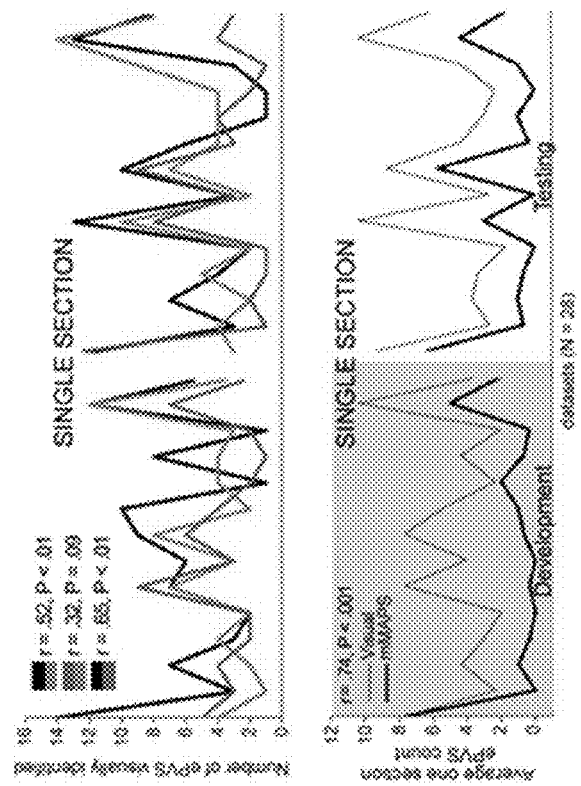
FIG. 5B: Data showing that visual count ratings correlated well with one another (top), as well as with the results of mMAPS (bottom) in single-section measurements. Blue line is that of the expert rater.
Figure 5C:
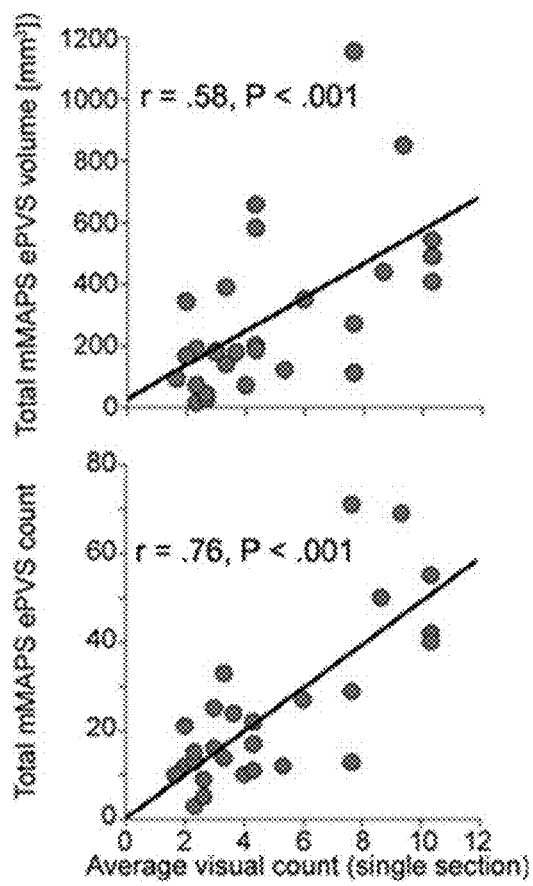
FIG. 5C: Data showing that single-section visual counts are correlated with total PVS volume, as measured with mMAPS (top) and total mMAPS ePVS count (bottom).

In this Example, all of the development datasets considered had a low ePVS burden; the single hemisphere with the highest count was between 1 and 11, corresponding to a categorical burden rating of 1 or "low" (see, Potter, G. M., et al., CEREBROVASC DIS, 2015. 39(3-4): p. 224-31). With respect to this categorical score, there was perfect inter-rater reliability (Cohen's kappa=1), as well as mMAPS's detection of likely ePVS in each of the slices rated. Because of this unexpectedly low variance, and to more precisely assess the algorithm's ability to detect likely ePVS, reliability estimates were assessed on the basis of counts. We report these values as well as the counts from each rater and mMAPS's detection of likely ePVS in FIG. 5B and FIG. 5C. The correlation of visual counts between raters was high, despite not being from the same slice (r=0.52, p<0.05; r=0.32, p<0.1; r=0.65, p<0.05, respectively, FIG. 5B). There was a very high correlation between counts by visual raters and mMAPS' detection of ePVS in the same slice (r=0.65, p<0.001; r=0.69, p<0.001; r=0.54, p<0.01) for each rater, respectively. The average visual counts and average mMAPS counts were more highly correlated (r=0.74, p<0.001), shown in FIG. 5B. With regard to visual ratings and whole-brain count consistency, average visual rating scores were highly correlated with automated detection of total burden volume (r=0.58, p<0.01) and total ePVS number (r=0.76, p<0.01, FIG. 4C).

Figure 5D:
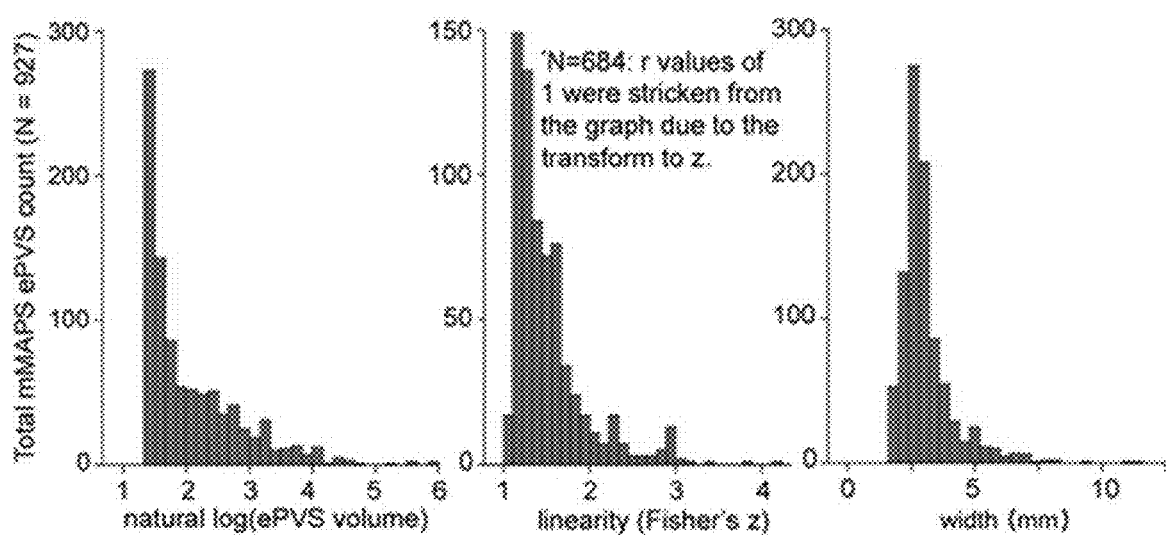
FIG. 5D: Data showing the distributions of volume (left), linearity (middle), and width (right) over mMAPS-identified ePVSs.

The morphology of detected ePVS across datasets is presented in Table 2 and FIG. 5D. The average number of ePVS per subject was 24.6 (range 3 to 71) and average total burden volume (SD) was 303.0 (267.74) mm3. Distributions of ePVS morphology features across all identified ePVS identified in Example 1 is visualized in FIG. 5D. The minimum width was 1.7 mm (one voxel width corner-to-corner), the maximum width ePVS detected across all datasets considered in Example 1 was 13.5 mm, and the average width of detected ePVS was 3.12 mm.

TABLE 2

Characteristics of PVS Identified per Data Set with mMAPS

| Characteristic | Mean ± Standard Deviation | Minimum | Maximum |
|---|---|---|---|
| Total cluster number | 24.6 ± 18.24 | 3 | 71 |
| Total PVS volume (mm$^3$) | 303.0 ± 267.74 | 15 | 1153 |
| Median width (mm) | 2.8 ± 0.23 | 2.3 | 3.2 |
| Maximum width (mm) | 6.2 ± 2.77 | 2.9 | 13.5 |
| PVS volume:PVS width | 3.0 ± 0.67 | 1.8 | 4.5 |

Figure 5E:
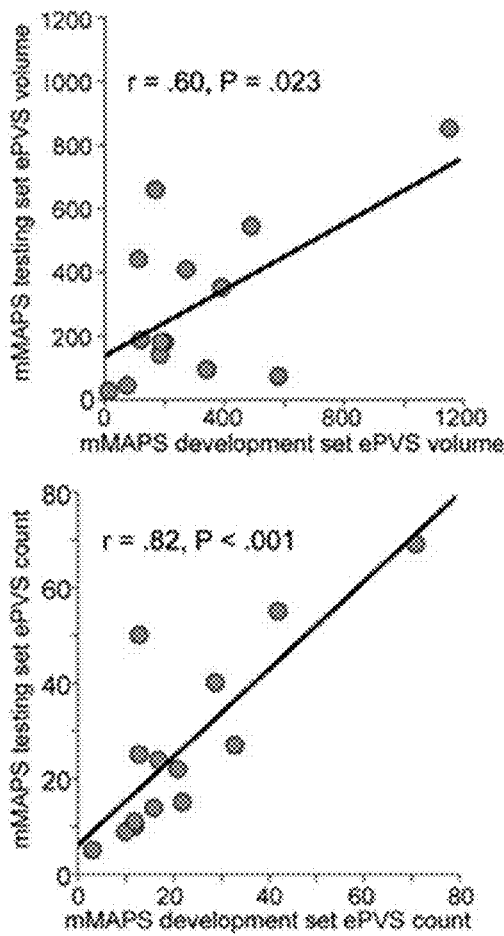
FIG. 5E: Signal-to-noise ratio (SNR) and CNR measurements, visual count ratings, and mMAPS results. (e) mMAPS measured were correlated between repeated measures of the same participants for total volume (top) and count (bottom).
Figure 5F:
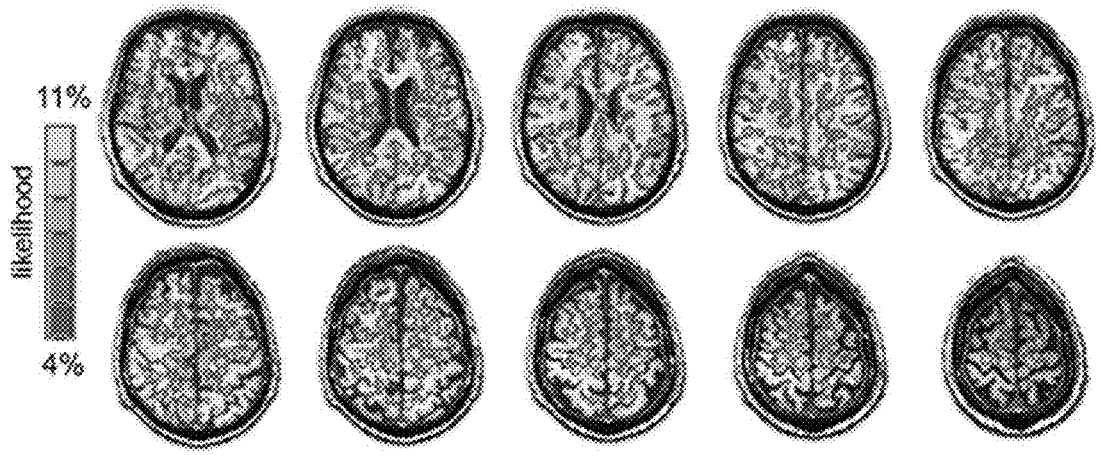
FIG. 5F: Data showing the spatial likelihood of the occurrence of an identified ePVS in participants overlaid on a representative T1-weighted volume.

In this Example, there was high intra-subject correspondence across repeat visits. There was a strong positive correlation between total cluster number and total volume between two annual study visits (r(12)=0.82, 0.60, respectively, p<0.05, FIG. 5E). No association of PVS counts, volume, or width and subject age was observed in this sample.

Type II errors observed were 1) contiguous ePVS that were shaped as an "H", i.e. two ePVS joined by an edge or corner due to partial volume effects on "normal" tissue between them and 2) ePVS which were located in an area of low contrast to noise, resulting in a less linear cluster than the de facto ePVS; these were eliminated on the basis of their non-linear morphology.

Discussion

This Example demonstrates the utility of an automated method for segmenting ePVS in commonly acquired clinical sequences at a field strength of 3T on a per-PVS basis. The disclosed method provides morphological (linearity, volume, width) information of each ePVS, as well as total burden volume, which has not previously been well established in the literature.

Estimated morphology resulting from the disclosed method is consistent with the existing literature. The median width detected in each subject dataset was 2.8 mm, with a range of 2.3 mm to 3.2 mm over all subjects considered in Example 1. This is consistent with established neuroradiological reports of ePVS having a diameter of usually less than 3-5 mm (Wardlaw, J. M., et al., LANCET NEUROL, 2013. 12(8): p. 822-38; Hernández, M. D. C. V., et al., JOURNAL OF MAGNETIC RESONANCE IMAGING, 2013. 38(4): p. 774-785), while still capturing highly linear structures, with the maximum detected ePVS width being 13.5 mm in this sample. The total burden volumes identified with these methods (mean=302 mm$^3$) is higher than total volumes reported by other groups. Previous work requiring manual correction for elimination of false positive voxels in the absence of cluster-specific morphological characterization (see, e.g., Ramirez, J., et al., J ALZHEIMERS DIS, 2015. 43(2): p. 415-24)—i.e., large (including those 5-15 mm in diameter) clusters that would be likely excluded on the basis of cross-sectional size—are included in the present method only if they also are highly linear. Highly linear structures that meet the intensity profile are likely dilated spaces, rather than lacunar infarcts (Wardlaw, J. M., et al., LANCET NEUROL, 2013. 12(8): p. 822-38), even for structures up to 15 mm in diameter (Hernández, M. D. C. V., et al., JOURNAL OF MAGNETIC RESONANCE IMAGING, 2013. 38(4): p. 774-785). The methods presented herein allow the user to modify minimum diameter and/or linearity thresholds. Recent studies employing high sensitivity imaging methods report much higher ePVS burden (Bouvy, W. H., et al., INVEST RADIOL, 2014. 49(5): p. 307-13; Bouvy, W. H., et al., J CEREB BLOOD FLOW METAB, 2016. 36(10): p. 1708-1717) than previous studies (Ramirez, J., et al., J ALZHEIMERS DIS, 2015. 43(2): p. 415-24; Chen, W., et al., AJNR AM J NEURORADIOL, 2011. 32(8): p. 1490-5). Additionally, the reported volumes are from whole-brain assessment, rather than strictly supratentorial WM, which has been used to delineate centrum semiovale (CSO) from other WM. The methods described herein would allow users to limit analysis to a specific region of interest, including CSO, specifically. When ePVS quantification is restricted to supratentorial WM, the mean volume detected is 104.4 mm$^3$, a value higher than but within the reported distribution range of previous work reporting total ePVS volume (Ramirez, J., et al., J ALZHEIMERS DIS, 2015. 43(2): p. 415-24).

When evaluated by visual rating methods, all datasets considered in Example 1 included had a categorical score of "mild" burden (Potter, G. M., et al., CEREBROVASC DIS, 2015. 39(3-4): p. 224-31). That is, assessment of the single axial slice through the CSO was between 1 and 10 on the hemisphere with the highest burden in that slice, resulting in a category score of 1. This category score was in perfect correspondence within raters and within mMAPS's ratings. While this narrow distribution represents a limitation in the assessment of the algorithm across burden levels, it does provide the opportunity to discuss the robustness of the methods with respect to sensitivity. Subsequent analysis of single slice cluster counts revealed a significant correlation between raters and mMAPS. Further, there was a strong, positive correlation between visual ratings and both counts and volumes extracted from the total brain, further supporting the use of these methods as a more robust assessment of whole brain burden. The ability of these methods to detect a distribution of ePVS burden in a sample that would have been categorically considered homogenous demonstrates the value of these methods in overcoming floor effects in the field (Gao, F. Q., et al., J ALZHEIMERS DIS, 2011. 26 Suppl 3: p. 379-88), and provides an opportunity to evaluate subtle differences in datasets, which is of particular value in longitudinal studies (van den Heuvel, D. M., et al., AJNR AM J NEURORADIOL, 2006. 27(4): p. 875-8).

In addition to providing an accessible method for discerning the spatial distribution of ePVS in WM, some implementations of a whole-brain algorithm such as mMAPS will substantially increase the dynamic range of burden measurements beyond that of single axial slice ePVS counts. In these 28 datasets, counts in the whole brain were approximately 7.1 times that of ePVS instances on a single slice, and volume (or area), a quantity that is generally not measured when assessing a single axial slice, represents a nearly 100-fold increase in the range of the measured proxy variable for burden. While studies on subjects with high burden do not suffer as badly from the low dynamic range of single slice counts, these studies are unlikely to capture early stages of pathologic change that might better inform investigations of the etiology of ePVS; if centrum semiovale or basal ganglia ePVS categorical measurements are used as proposed by Potter et al. (Potter, G. M., et al., CEREBROVASC DIS, 2015. 39(3-4): p. 224-31), range of burden severity becomes further truncated to five discrete categories. For example, the data presented in Example 1 would have zero variance (all subjects would be categorized as a "1" under the categorical burden scale, having between 1-10 identified PVS), which would preclude the possibility of statistical comparisons with semi-continuous variables that may be correlated or causative, such as age or blood pressure.

As presented above, the algorithm is built upon two separate computational steps, the first being based on signal intensity, the second based on 3D fitting of clusters of interest. While some datasets may have sequences that are not employed in the described methods, which limits the generalizability of this method, there is a precedent for extracting volumetric estimates of ePVS burden with fewer sequences (Ramirez, J., et al., J ALZHEIMERS DIS, 2015. 43(2): p. 415-24). With sufficient resolution, it is reasonable that the morphological fitting component of this algorithm could be applied to clusters identified in single- or two-sequence datasets. Similarly, the increased resolution and signal-to-noise provided by refined sequences and/or increased field strength would serve to further increase the robustness of these methods. Partial volume effects inherent in any digitized imaging modality introduce an unavoidable amount of uncertainty in estimating the true diameter or volume of any body of interest, including ePVS (Bouvy, W. H., et al., INVEST RADIOL, 2014. 49(5): p. 307-13). Smaller voxel sizes would increase the certainty of estimating the true width of the ePVS, and may allow detection of non-dilated PVS (Bouvy, W. H., et al., J CEREB BLOOD FLOW METAB, 2016. 36(10): p. 1708-1717).

This study design also was limited by the assessment of ePVS in white matter structures only, as the ability to detect ePVS in basal ganglia structures is also of interest. Although the reliability of these methods in the basal ganglia region is yet to be established, it is likely that they will be similar, as the relative intensity of ePVS is isointense to CSF in this region as well. Morphological constraints may need to be optimized to include larger diameter ePVS in this area, however (Wardlaw, J. M., et al., LANCET NEUROL, 2013. 12(8): p. 822-38).

While the additional information provided by simultaneous consultation of multiple sequences can increase sensitivity and specificity of ePVS segmentation, because of the small size of ePVS, errors of misregistration across sequences can be a major source of error. Similarly, failure to successfully segment white matter from gray matter can result in errors, as errant inclusion of voxels at the gray/white cortical interface may have a similar intensity profile as ePVS. Particularly in cases of very high burden, misclassification of PVS as non-brain during white matter extraction can result in errors of omission. For these reasons, as in any automated analysis, visual confirmation of successful co-registration and final results are stressed.

Although increasing age has been reported as a correlate of ePVS burden, this has been in cases of very high burden assessed by visual rating (Yakushiji, Y., et al., NEUROLOGY, 2014. 83(23): p. 2116-23). In reports using very high field strengths, the correlation with age has been revealed to be an insignificant contributor to ePVS burden, particularly in the white matter (Bouvy, W. H., et al., J CEREB BLOOD FLOW METAB, 2016. 36(10): p. 1708-1717.). It is not particularly surprising, then, that in our relatively healthy (low ePVS burden) cohort, a relationship with age was not observed. Application of this algorithm in a cohort of high-burden subjects is certainly warranted.

Various techniques utilized in this Example identify typical ePVS on the basis of fit to models. We identified two ways in which these constraints were the source of errors. In areas that have low contrast-to-noise, the segmentation can fail to define the border of the ePVS. This failure results in a large cluster (or a cluster having low linearity) that is subsequently eliminated on the basis of morphology. When this occurred, it tended to be at areas of cortex far from the isocenter of the head coil near gray/white matter boundaries. This limitation might be remedied with the acquisition of images of higher spatial resolution, higher contrast-to-noise ratio, or with more accurate shimming. Second, various techniques utilized in this Example refrain from defining clusters that are bridged by a voxel that results from partial volume effects (clusters that are shaped as an "H"). While this may be remedied by resampling the data into smaller voxels, such treatment of the data could lead to errant inclusion of voxels that are not truly representative of ePVS. Alternatively, an additional layer of cluster processing, such as one using a watershed method to separate contiguous clusters (Eddins, S. THE WATERSHED TRANSFORM: STRATEGIES FOR IMAGE SEGMENTATION. TECHNICAL ARTICLES AND NEWSLETTERS 2002 [cited Jan. 3, 2017], available at https://www.mathworks.com/company/newsletters/articles/the-watershed-transform-strategies-for-image-segmentation.html), may prove fruitful. Again, higher resolution imaging would likely not be susceptible to this limitation.

As discussed above, limitations of this method include 1) the need for closely aligned, multi-contrast datasets, 2) uncertainty in volume estimates resulting from partial volume effects present in radiological methods, and 3) current validation limited to white matter structures. An additional limitation of the study design is the use of datasets that were retrospective, which necessitated using parameters that were not optimized for identifying ePVS, specifically. The use of optimized sequences could reduce the number of contrasts needed and more closely approximate the true burden.

Example 2—Application to Image Data from a Single Volumetric Scan Having Two Sequences Abstract In this Example, an alternate embodiment of the method for segmenting and characterizing enlarged perivascular spaces (ePVS, "Virchow-Robin spaces") in white matter is described. While it has been shown that four differently weighted MRI images ($T_1$, $T_2$, FLAIR, and proton density) may be used to characterize ePVS in humans in a robust and unbiased manner, the time necessary to acquire all four weightings utilized for ePVS definition in Example 1 may be prohibitive in non-research settings. Described herein is a method for the identification of probable ePVS using only a $T_1$ and FLAIR at clinical-strength MRI which uses similar morphological constraints to eliminate Type I error as used in the four-MRI-sequence approach described in Example 1. An advantage of this approach is that it makes the ePVS detection method accessible to groups which currently have large sets of limited data. A comparison of the limited sequence algorithm to method described in Example 1 and to visual ratings from three raters in the same dataset is presented.

Introduction

Virchow-Robin spaces which are visible on standard magnetic resonance imaging protocols at clinical field strength have been termed enlarged perivascular spaces (ePVS). These fluid-filled spaces, which follow patterns of vasculature in white matter, have recently been grossly associated with several neurological disease processes. The detection of ePVS in MR imaging has classically included the necessity of visually inspecting both $T_1$ and $T_2$-weighted sequences to ensure that the space in question is isointense to ventricular cerebrospinal fluid. Manual ePVS burden assessment can be onerous and time-consuming in clinical and in research settings, which may preclude whole brain assessment, and is typically done on axial images for which burden can vary based on the position of the slice and the orientation of vascular structures at that position. An automated method that utilizes spatially co-registered $T_1$, $T_2$, FLAIR and proton density (PD) for whole brain burden assessment is described in Example 1, but the time frame for acquisition of all four sequences may be prohibitive in clinical or research settings. The requirement of four separate contrasts may also preclude the use of the multimodal algorithm in retrospectively derived datasets, which are of particular interest in the context of neurodegenerative disease and normal aging. Finally, movements between sequences that are more than one millimeter and/or imperfect post hoc co-registrations may limit the sensitivity of the mulitimodal algorithm. ePVS detection is particularly vulnerable to small errors in coregistration due to the linear shape and small size of ePVS. An algorithm requiring fewer sequences increases sensitivity by requiring less coregistration and interpolation while shorter acquisition time minimizes opportunities for subject motion to compromise data.

These limitations motivate an alternate implementation of the disclosed ePVS detection technique that uses fewer volumes or weightings, or even a single volume or weighting, as a basis set. The most commonly acquired weighting performed at clinical MRI field strengths are $T_1$ and $T_2$. This Example 2 describes a segmentation algorithm that utilizes $T_1$ and $T_2$-weighted FLAIR volumes (MAPS-$T_1$) and compares results in a repeated measures cohort to expert visual ratings, as well as a separate multisite validation of MAPS-$T_1$ in the publicly available Alzheimer's Disease Neuroimaging Initiative (ADNI) cohort. Described herein is a method for identification of enlarged perivascular spaces using only commonly clinically acquired $T_1$ and FLAIR MR imaging, making the algorithm accessible to groups with valuable sets of limited data.

Methods

Participants: Cohort One-Repeated Measures:

Neuroimaging data were acquired as part of an ongoing prospective research study. Study participants signed informed consent and HIPAA authorization, approved by the Institutional Review Board, prior to participation in the study. Neuroimaging sessions were performed during two distinct sessions on 14 participants (Table 3, characteristics of cohort one are at visit one). The mean inter-scan interval was 366 days (range: 280-441 days, st. dev.=49). Participants were older dementia-free adults living independently. Visual ratings were made by three independent raters on each dataset using an established visual rating scale (Wardlaw, J. M., et al., LANCET NEUROL, 2013. 12(8): p. 822-38). One rater is a board certified neuroradiologist with 10.5 years of experience and the other two raters each have at least 10 years of MRI experience. Spatially co-registered $T_1$-weighted and FLAIR images were made available and each rater chose an axial slice superior to the lateral ventricles that subjectively represented the slice with the highest number of ePVS. Each rater identified the location of each distinct ePVS on the entire slice by drawing a single pixel region of interest. Segmented ePVS were overlaid on $T_1$-weighted and FLAIR volumes for each subject and an author (DLS) screened the results for false alarms.

TABLE 3

Dataset Characteristics

|  | Cohort 1 (N = 14) | Cohort 2 (N = 30) |
|---|---|---|
| Age, years (range) | 85.3 (70-101) | 74.3 (58-92) |
| Gender (% female) | 57.8 | 40.0 |
| MMSE (range) | 28.36 (22-30) | n/a |
| CDR % 0 (range) | 83 (0.0-0.5) | 16.7 (0.0-2.0) |
| ICV (cm$^3$) | 1871.6 ± 202.8 | 1855.4 ± 219.1 |
| WMH (cm$^3$) | 12.3 ± 10.2 | 10.5 ± 10.1 |
| Hachinski % >0 (range) | 64 (0-8) | 90 (1-3) |
| History of stroke (%) | 29 | 7 |

Participants: Cohort Two-ADNI:

Thirty datasets that was acquired as part of the multisite ADNI2 imaging protocol were downloaded as a part of a larger cohort from the ADNI website subject to the following constraints: 1) near isotropic $T_1$-weighted and FLAIR MRI, 2) Hachinski Ischemia Score (HIS) >0 and clinically reported presence of hypertension, 3) age was normally distributed in the cohort (range: 58-92 years, Table 1). Seventeen sites were represented in the final dataset. Segmented ePVS were overlaid on $T_1$-weighted and FLAIR volumes for each subject and two authors (ELB and DLS) screened the results for false alarms.

Image Acquisition and Preprocessing:

Cohort one MRI data were obtained using a 3.0T Siemens Trio MRI (TIM Trio System, Siemens Healthineers, Erlangen, Germany). Two sequences were acquired: 3D $T_1$-weighted magnetization prepared rapid gradient echo ([MPRAGE/$T_1$]: TR/TE/TI/FA=2300 ms/3.41 ms/1200 ms/12°, 128 sagittal 1 mm slices with no gap, FOV=256× 192 mm, imaging matrix=256×192); 2D fluid attenuated inversion recovery ([FLAIR]: TR/TE/TI/FA=9000 ms/87 ms/2500 ms/100°, 95 axial 2 mm slices with no gap, FOV=228×248 mm, imaging matrix=236×256, 2 averages). Cohort 2 MRI data were acquired as described at http://adni.loni.usc.edu/methods/mri-tool/mri-analysis/.

DICOM files were converted to NIFTI using mcverter (MRIConvert, http://lcni.uoregon.edu/downloads/mriconvert/mriconvert-and-mcverter). $T_1$-weighted images were segmented into tissue types using Freesurfer v5.1, which yielded masks of white matter (WM), cortical gray matter (GM), subcortical gray matter (BG), and ventricular CSF. WM masks were corrected for tissue misclassification due to white matter hyperintensities (WMH), meaning that WMH were included in the WM mask, by the method described in (Promjunyakul, N., et al., NEUROIMAGE CLIN, 2015. 8: p. 224-9). Briefly, clusters of contiguous voxels of intensity 35% higher than the peak of the distribution of intensities in FLAIR WM were used as seed clusters for a custom cluster growing algorithm. The mean intensity of each cluster was calculated and then all nearest neighbor voxels of intensity exceeding 95% of the mean cluster intensity were iteratively added to the cluster until no additional voxels met threshold. White matter masks were eroded by a single voxel to avoid the potential of partial volume effects. Separately, FLAIR and $T_1$ volumes were bias field corrected using slicer3 (https://www.slicer.org/) in preparation for ePVS segmentation. The MAPS-$T_1$ algorithm was accomplished in two phases, intensity-based and morphology-based, as follows.

Local Voxel Intensity Inhomogeneity and Cluster Morphology Model.

Figure 6:
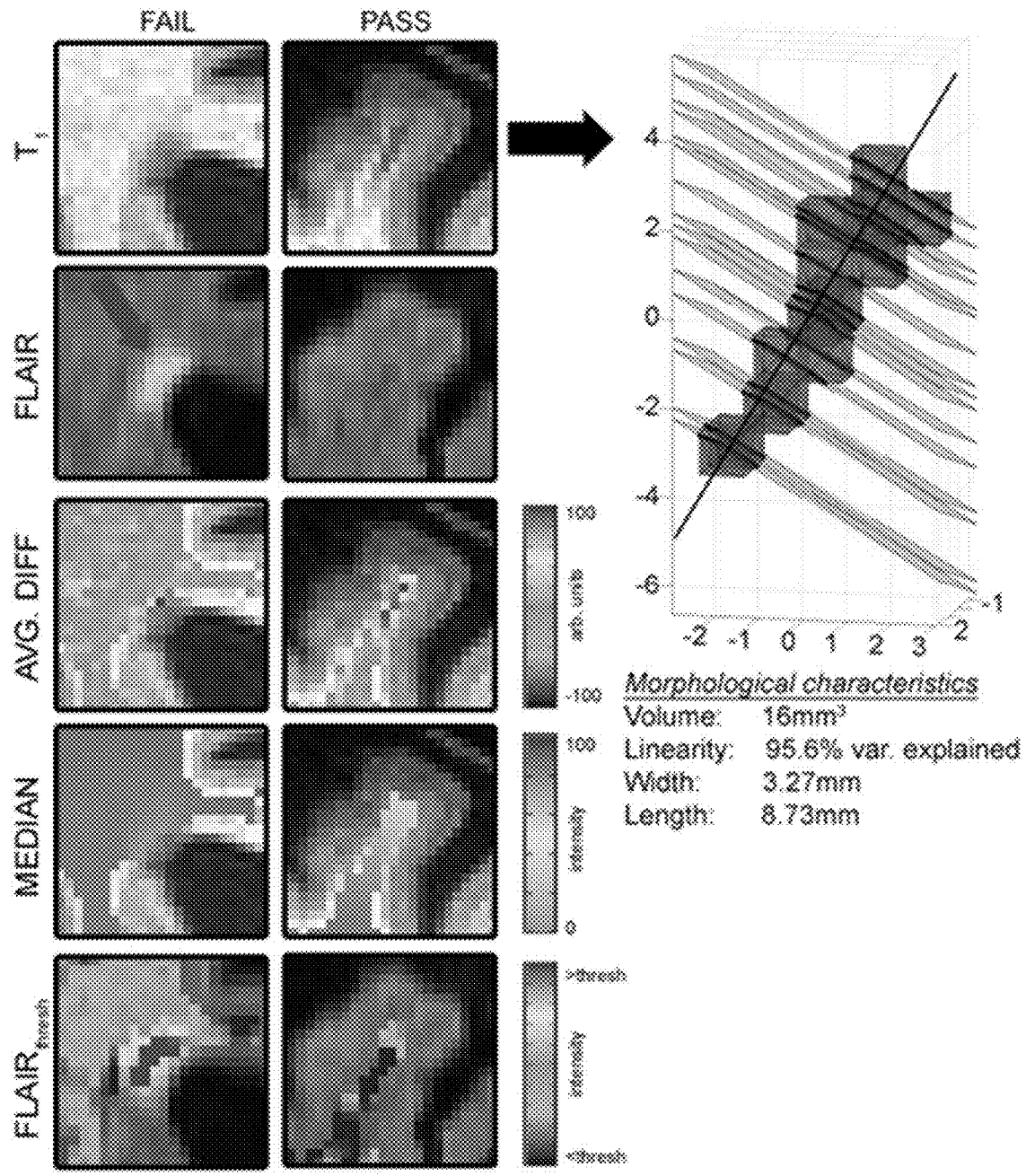
FIG. 6: A graphical example showing a periventricular FLAIR-screened object that resembles an ePVS but is a WMH edge (left, "FAIL") and a successful segmentation of an ePVS in the superior frontal gyrus (right, "PASS"). The isolated cluster is submitted to the morphological constraint (far right).

The general flow of processing is depicted in FIG. 6. $T_1$ and FLAIR data were preprocessed as in Example 1. A local intensity variability model to identify candidate voxels belonging to an ePVS was defined as follows. For voxels within the white matter (WM) mask, the local homogeneity of each voxel is assessed to identify clusters of interest. Specifically, in the $T_1$-weighted images, a search field was defined as all voxels within 3.5 mm from the ith voxel and within the WM mask. The median intensity value of voxels in the search field neighborhood is computed and recorded as the ith voxel's median score. Separately, the mean difference between the ith voxel and its neighbors in a field of radius 5.5 mm was calculated (its "difference score"). In order for a voxel to meet criteria for a likely ePVS on isotropic $T_1$-weighted images, it must a) have an intensity that is less than 90% of the median score, b) be in the WM mask, and c) have a difference score that is larger than 5% of its intensity value. Each of these thresholds are generally governed by the SNR of the data and CNR of ePVS relative to normal appearing white matter (NAWM), respectively, and may be changed if data are noisy or if the weighting is tuned such that ePVS are less visible in contrast to NAWM. Separately, voxels that met criteria for being non-white matter hyperintensity on FLAIR were those for which the FLAIR intensity was lower than the sum of the mean and standard deviation of all voxels in the WM mask. The voxels that met both the FLAIR and the $T_1$ criteria were considered to be candidate voxels and were constructed into voxel clusters larger than 5 (corners touching). Those clusters were submitted to the morphological constraint model.

The morphological constraint was largely the same as was previously described in Example 1, with the exception of a minimum cluster size and calculation of linearity and the width of the cluster. The minimum cluster size was set at 5 voxels with corners touching in order to ameliorate issues with calculating linearity of some clusters (i.e. the likelihood of a configuration of 5 voxels being collinear with respect to a best fit line through a longitudinal axis is much smaller than that of 4 voxels). Linearity was defined as the percent explained variance of the fit longitudinal vector; the inclusion constraint was set at >80%. The width calculation was redefined as the maximal distance between vertices that describe the intersection of a plane that is normal to the fit longitudinal vector (used in the linearity calculation) for each cluster and upon which the center of a voxel lies. This plane was constructed for each voxel in each cluster (see the set of green planes in the right-hand image of FIG. 6), and maximal vertex distances calculated, the largest of which defined the width of the cluster; clusters with a larger width than 15 voxels (16.41 mm, corner to corner) were excluded. The length of the cluster was calculated as the furthest distance between intersected vertices on the fit longitudinal vector; there were no inclusion or exclusion criteria for length.

Statistical Analysis.

The performance of this segmentation algorithm was evaluated relative to visual counts in each dataset by three raters in cohort one. Reported correlations of manual counts are the average counts over three raters; in the case of the automated algorithm, average counts were assessed in the slices which were visually rated. In an effort to report the unedited result of the automated algorithm, these visual validation metrics were calculated on the output of MAPS-$T_1$ before manual removal of false alarms. Within-subject false alarm rate was calculated by dividing the number of false alarms in a subject's dataset by the total number of objects segmented by the algorithm. Signal-to-noise ratio (SNR) and ePVS contrast-to-noise (CNR) for both $T_1$-weighted and FLAIR volumes were also calculated.

Statistical analysis of cohort two results included the calculation of within-subject false alarm rates, SNR and ePVS CNR for both $T_1$-weighted and FLAIR volumes, and count and volume summary variables for each subject. ePVS SNR and CNR were calculated on true positives only.

Positive predictive value was calculated for both cohorts over all segmented ePVS considered in Example 2. SNR for $T_1$ and FLAIR was calculated as the mean intensity of identified ePVS or NAWM divided by the standard deviation of NAWM. CNR measurements were calculated as the absolute value of the difference between the mean of identified ePVS and NAWM (i.e. a volume from which segmented ePVS and hyperintense FLAIR voxels were subtracted) and divided by the standard deviation of NAWM.

Results Cohort One:

Visual ePVS counts were significantly correlated with MAPS-$T_1$ ($r_{(26)}$=0.72, p<0.0001). Correlations between repeated measurements were significant for both methods in the single visually-rated slice (MAPS-$T_1$: $r_{(12)}$=0.87, p<0.0001, visual: $r_{(12)}$=0.86, p<0.0001) and for whole brain assessment (MAPS-$T_1$: $r_{(12)}$=0.77, p=0.001).

Figure 7A:
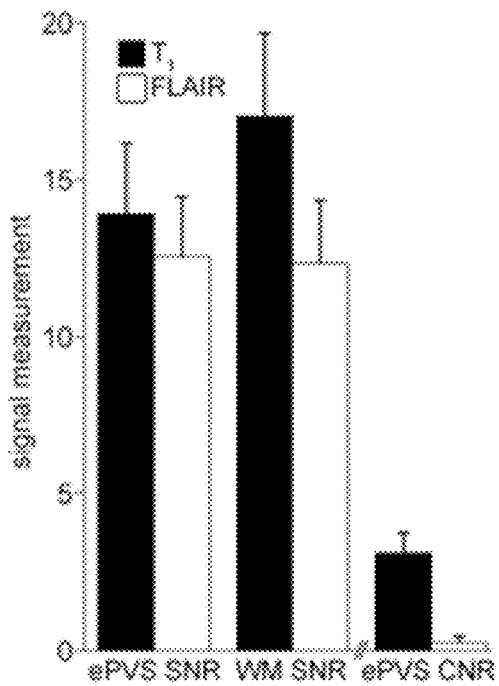
FIG. 7A: A set of bar graphs of measurement of SNR (signal-to-noise ratio) and CNR (contrast-to-noise ratio) for T1 and FLAIR datasets in Cohort 1.
Figure 7B:
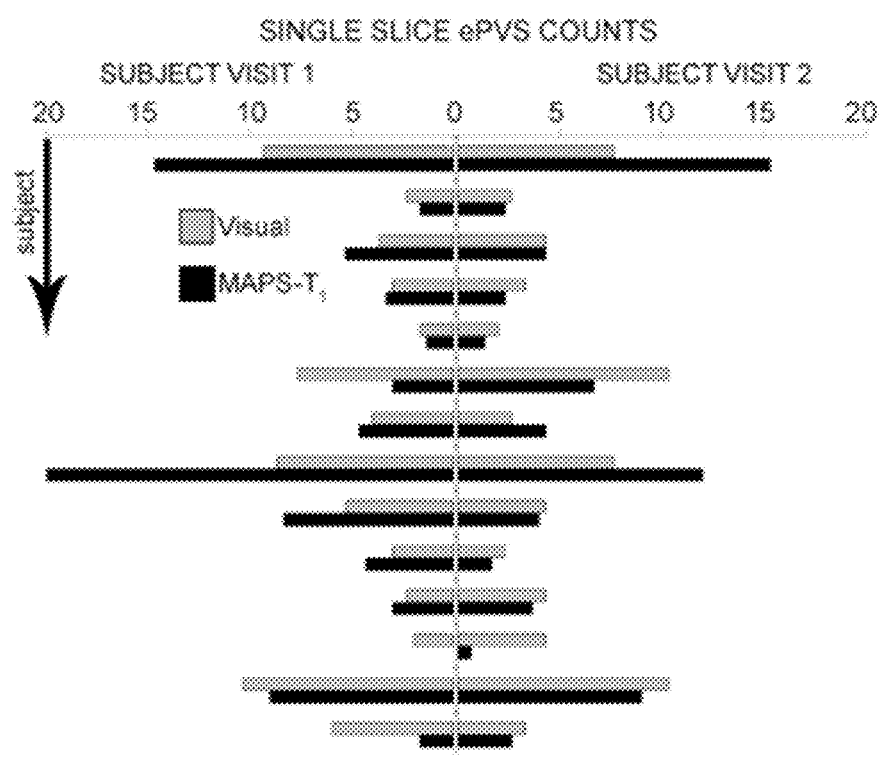
FIG. 7B: Graphical depiction of the average of single slice counts by visual raters (gray) and single slice MAPS-T1 counts for each of a cohort of 14 subjects.
Figure 7C:
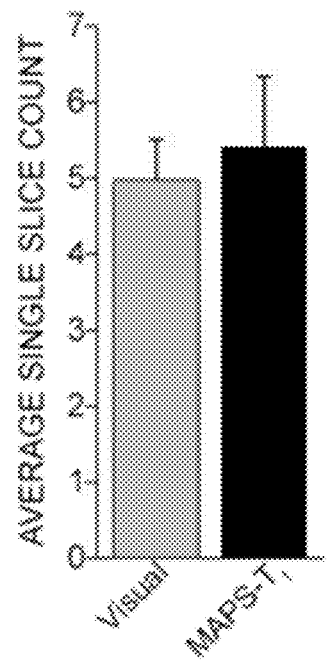
FIG. 7C: Bar graph showing single slice count averages over subjects when performed by visual or MAPS-T1 analysis (error bars show standard deviation).
Figure 7D:
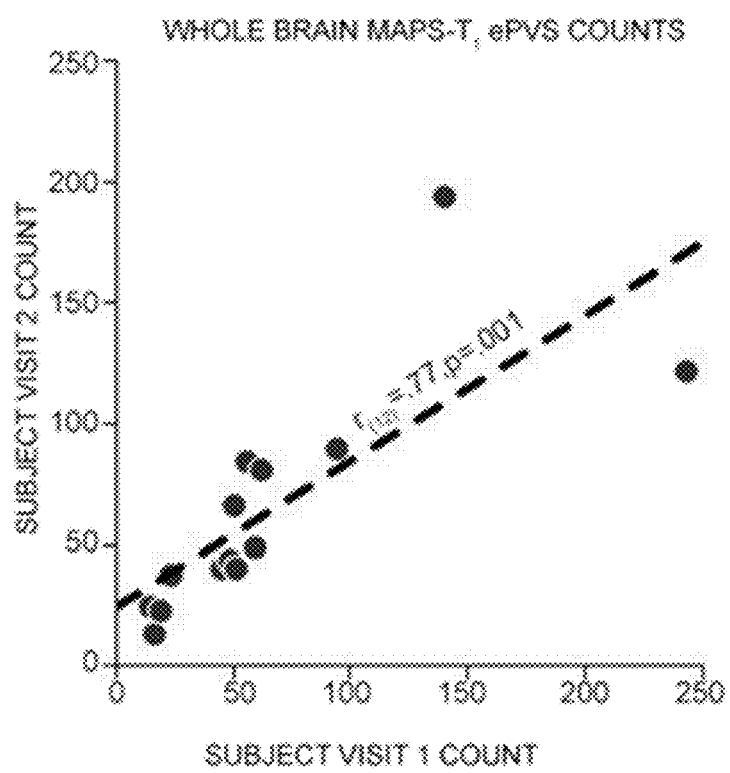
FIG. 7D: Plot of results within subject correlation for whole brain ePVS counts using MAPS-T1
Figures 7E, 7F:
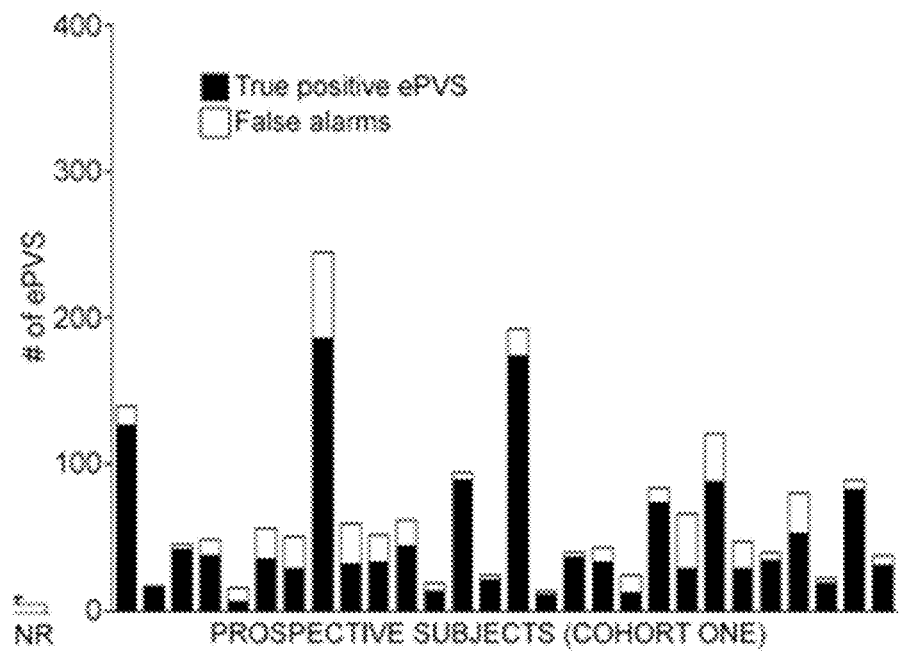
FIG. 7E: Bar graph showing true positive and false alarm rates for MAPS-T1 ePVS counts in Cohort one.
FIG. 7F: A set of bar graphs of measurement of SNR (signal-to-noise ratio) and CNR (contrast-to-noise ratio) for T1 and FLAIR datasets in Cohort 2.
Figure 8:
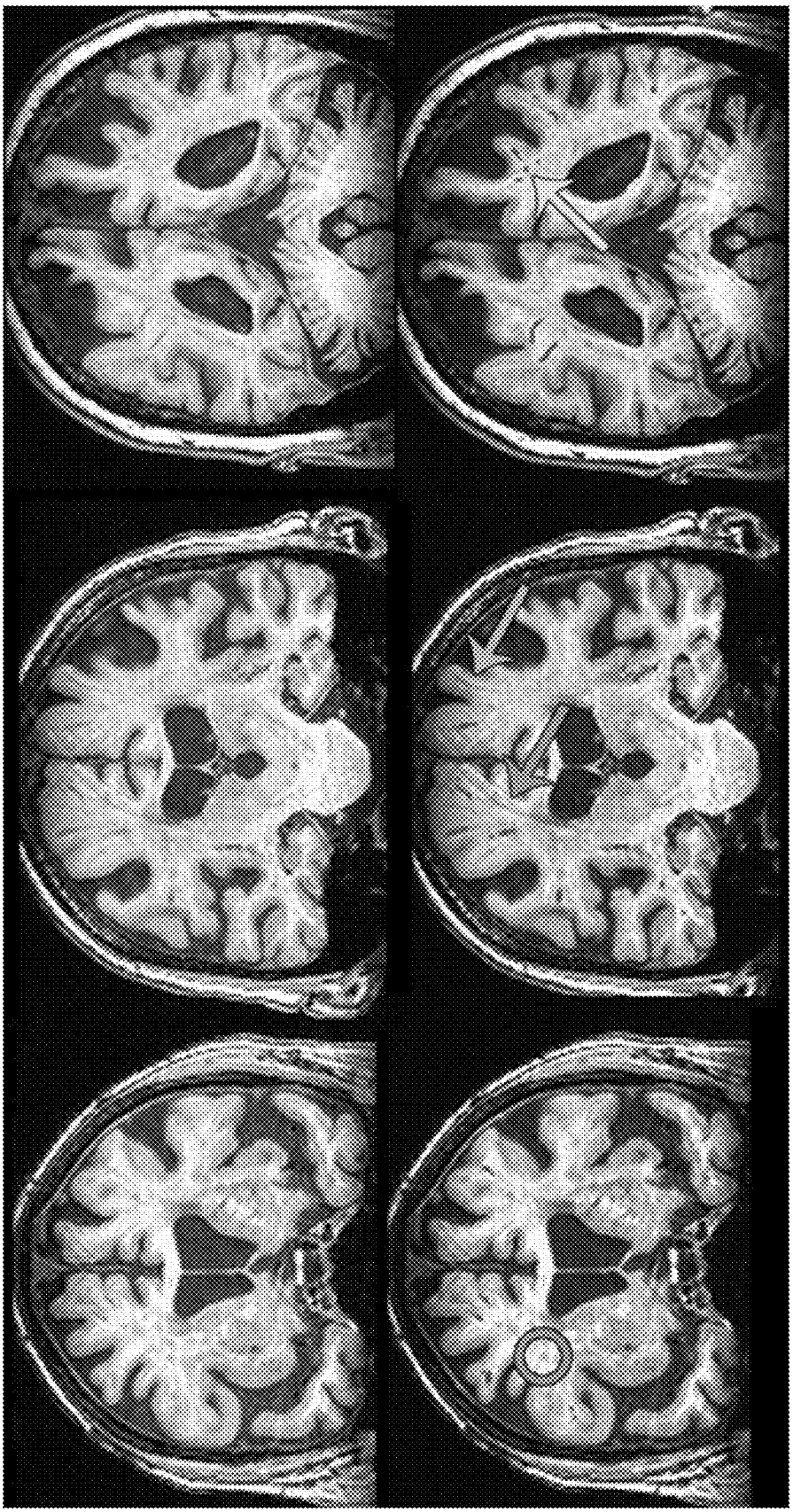
FIG. 8: A representative segmentation where the top row shows a set of T1-weighted images and the bottom row shows results of segmentation in red. Green circle=a deep WMH that has been avoided by the algorithm; green arrow=motion artifact avoided by the algorithm; blue arrow=a "missed" ePVS; yellow arrow=an example of the advantage of a three dimensional algorithm (3 ePVS oriented AP are identified proximal to an ePVS oriented obliquely in the coronal plane).

FIG. 7A shows a comparison of SNR and CNR measurements for $T_1$ and FLAIR. $T_1$ ePVS and NAWM SNR mean (st. dev. over datasets) were 13.9 (2.2) and 17.0 (2.7), respectively. FLAIR ePVS and NAWM SNR mean (st. dev. over datasets) were 12.5 (1.9) and 12.3 (2.0), respectively. $T_1$ and FLAIR ePVS CNR mean (st. dev.) were 3.1 (0.6) and 0.3 (0.2), respectively. FIG. 7B shows a comparison of single slice ePVS counts between a first and second visit, as assessed by either visual counting or the MAPS-$T_1$ analysis, for the 14 subjects in Cohort one. FIG. 7C shows single slice average counts over all subjects considered in Example 2 by either visual counting or the MAPS-T1 analysis (error bars are st. dev.). FIG. 7D shows the within subject correlation over two visits for whole brain ePVS counts using MAPS-$T_1$. FIG. 7E shows true positive ePVS counts and false alarm counts over the two visits for the 14 subjects of Cohort one using the MAPS-$T_1$ approach. The mean subject-wise false alarm frequency (st. dev., [range]) was 25% (16%, [6-56%]), which corresponded to an overall positive predictive value in cohort one of 77.5%. An example segmentation, with highlighted correct rejections and an example of a "miss", is shown in FIG. 8.

Figure 7G:
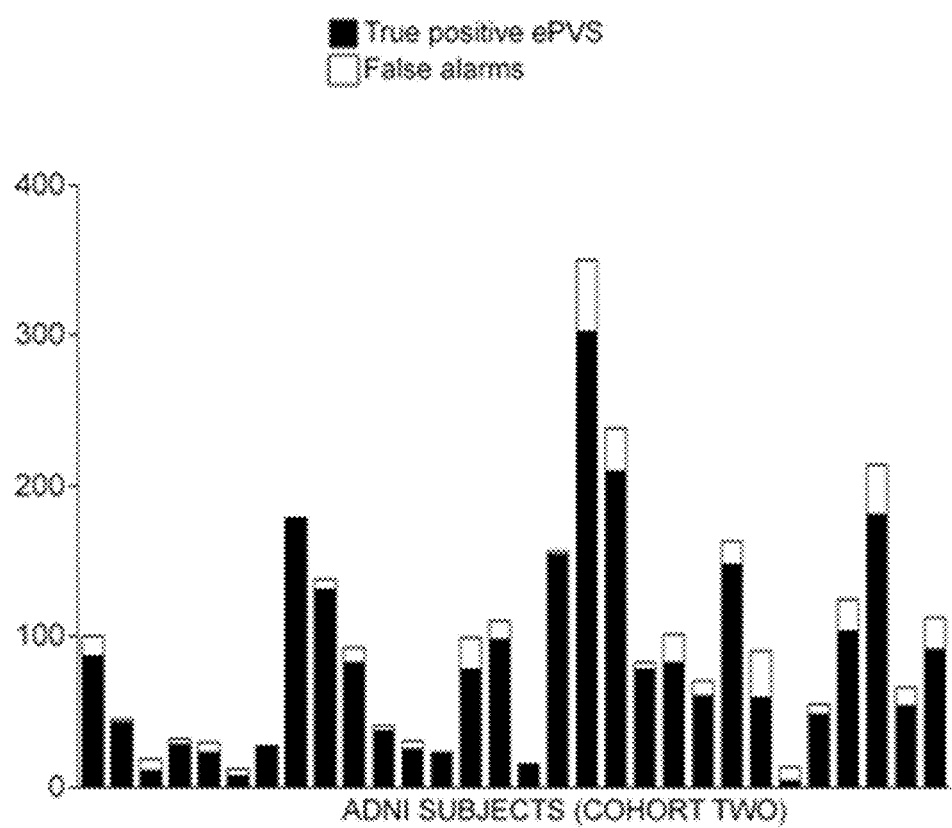
FIG. 7G: Bar graph showing true positive and false alarm rates for MAPS-T1 ePVS counts in Cohort two.

Cohort Two:

FIG. 7F shows a comparison of SNR and CNR measurements for $T_1$ and FLAIR for Cohort two. $T_1$ ePVS and NAWM SNR mean (st. dev. over datasets) were 9.5 (2.2) and 11.8 (2.5), respectively. FLAIR ePVS and NAWM SNR mean (st. dev. over datasets) were 11.0 (2.3) and 10.8 (2.4), respectively. $T_1$ and FLAIR ePVS CNR mean (st. dev.) were 2.3 (0.5) and 0.2 (0.2), respectively. FIG. 7G shows true positive ePVS counts and false alarm counts for the 30 subjects of Cohort two using the MAPS-$T_1$ approach. The mean subject-wise false alarm frequency (st. dev., [range]) was 15% (13%, [0-61%]; note that the Cohort two subject with the highest error rate had a relatively low overall burden, the stacked bar sixth from the right in graph in FIG. 7G), which corresponded to an overall positive predictive value in Cohort two of 87.5%.

Discussion

This Example 2 presents a method of segmenting ePVS based on the relative intensity of a voxel's neighbors and the morphological properties of isolated clusters on $T_1$-weighted imaging using hyperintensity on FLAIR as a rule-out. Comparison of the burden metric (ePVS counts) in a single slice to gold standard visual assessment yields significant and reliable estimates over repeated acquisitions <2 years apart. The choice of the modifiable thresholds for search fields, voxel median score (in these data, 10% smaller than the median) and mean difference score (5%) are driven by NAWM homogeneity, SNR, and ePVS CNR, respectively, and different thresholds may easily be chosen and implemented on a dataset-wide basis, though the settings used in this analysis appeared to be applicable to subjects with a wide range of WM pathology and spatially variable SNR and CNR, as well as in a separately acquired and analyzed multisite cohort from ADNI. These thresholds were chosen after qualitatively acceptable segmentations on the "SUBJECT VISIT 1" subset (FIG. 7, top middle left graph, left side). The maximum volume of the search field is informed by NAWM homogeneity in a dataset; if tissue homogeneity is very low (as in data for which $B_1$ inhomogeneity is high), the search field may be reduced, though minimum search field volumes are constrained by the physiological size of ePVS. The FLAIR is used for the screening of WMH that are falsely identified on $T_1$ as putative ePVS due to their similar hypointensity relative to NAWM (Pantoni, L., LANCET NEUROL, 2010. 9(7): p. 689-701); manually edited WMH masks can be applied in place of the voxelwise FLAIR constraint, though these masks may remove ePVS that are proximal to or contained by a WMH.

There have been several recently published articles describing various methods for automated or semi-automated ePVS segmentation on MRI. Reliable segmentation of these structures with clinically relevant sensitivity and specificity can be difficult owing to their small size relative to standard clinical imaging voxel sizes, low CNR compared to surrounding NAWM, morphological discontinuity due to both physiological variability and to partial volume effects, and shared intensity profiles over some or all commonly acquired MRI weightings with other MRI-visible pathology such as lacunar infarcts and WMH. Some methods have overcome many of these obstacles by utilizing high field (7 Tesla) acquisitions, machine learning, binary classifiers, Frangi- or object-based filtering, or software designed for lesion exploration that has been modified to detect ePVS. These methods appear to have some measure of success when comparing them to categorical visual ratings. The techniques described herein in Example 2 are relatively accessible compared to approaches which may be less relevant in the clinical context (e.g. high field acquisition or acquisition with specialized hardware a la the Human Connectome Project), due to other methods being computationally expensive, requiring a considerable amount of human interaction, being study-specific (i.e. classifiers and optimization schemes in machine learning paradigms are often driven by within-study data), or perhaps most importantly requiring multiple acquisitions (i.e. $T_2$-weighted spin echo and/or proton density) that may not be acquired as a matter of course. Notably, Example 2 omits analysis of ePVS that are located in the basal ganglia or in the midbrain, two regions which can exhibit high burden in aged brains; various techniques described herein with respect to Example 2 specifically rely on local intensity contrast which is different in subcortical gray matter and in the brainstem, and can vary widely across subjects and acquisition parameters due to heavy metal concentration in the basal ganglia and substantia nigra, especially in the aging population.

Error Assessment and Methods Comparison:

The method disclosed herein overcomes potential errors resulting from requisite voxelwise assessment in >2 separately acquired MRI contrasts. Coregistration between sequences that have been acquired with different weightings can be inaccurate; the width of ePVS can be as small as 1 mm, and slight errors in coregistration can result in reduced sensitivity when implementing algorithms using this approach. A more logistical concern is that multiple sequences may not be available in legacy data, and may be precluded by scan time constraints in prospective experiments. High resolution (1-2 mm isotropic voxels) $T_1$ and FLAIR weighted data can each be acquired in less than 5 minutes, reducing the effects of motion, which can be substantial in aged subjects in whom this algorithm is often applied. Using two commonly acquired sequences alleviates some concerns related to registration and the necessity of multiple weightings in a single subject, making this segmentation algorithm more widely applicable.

Any algorithm used to assess WM ePVS will suffer from incomplete or imperfect white matter segmentations. Many intensity-based tissue-type segmentation algorithms, including Freesurfer, have difficulty classifying non-NAWM, and older subjects who may be more likely to have a larger number of ePVS are more likely to have a higher burden of non-NAWM than younger subjects. The Example 2 shown here uses custom software (Promjunyakul, N., et al., NEUROIMAGE CLIN, 2015. 8: p. 224-9) to correct defects due to white matter hyperintensities (on FLAIR or $T_2$, and hypointense on $T_1$) in white matter segmentations. However, partial volume effects inherent in MRI can smooth white matter hyperintensity/NAWM and NAWM/gray matter interfaces, especially in cases of marked neocortical atrophy which can make the cortical ribbon difficult to delineate from NAWM. Often, false positive errors are made at these interfaces; thin clusters that track the interface are identified as possible ePVS and will pass the morphological constraint. A specific false positive has been observed in datasets for which the posterior horn of the lateral ventricle is not contiguous with the rest of the lateral ventricle; in the absence of partial volume effects, ePVS are by definition isointense to cerebrospinal fluid and these objects are shaped as an elongated teardrop. Often this structure is incorrectly classified as white matter by automated tissue segmentation algorithms and so is identified as a relatively large ePVS.

ePVS can occur in clusters following the course of penetrating vessels and appear as such in elderly without other signs of disease. As with other ePVS segmentation algorithms, if ePVS are closely grouped in such a way that partial volume effects cause them to appear as a large cluster of heterogeneous intensity, the object will be removed as insufficiently linear. However, if there is sufficient resolution, contrast-to-noise, and NAWM between individual ePVS, they may be properly segmented with this algorithm even though they may be quite close to one another (<2 mm, see FIG. 8, yellow arrow).

Figure 9:
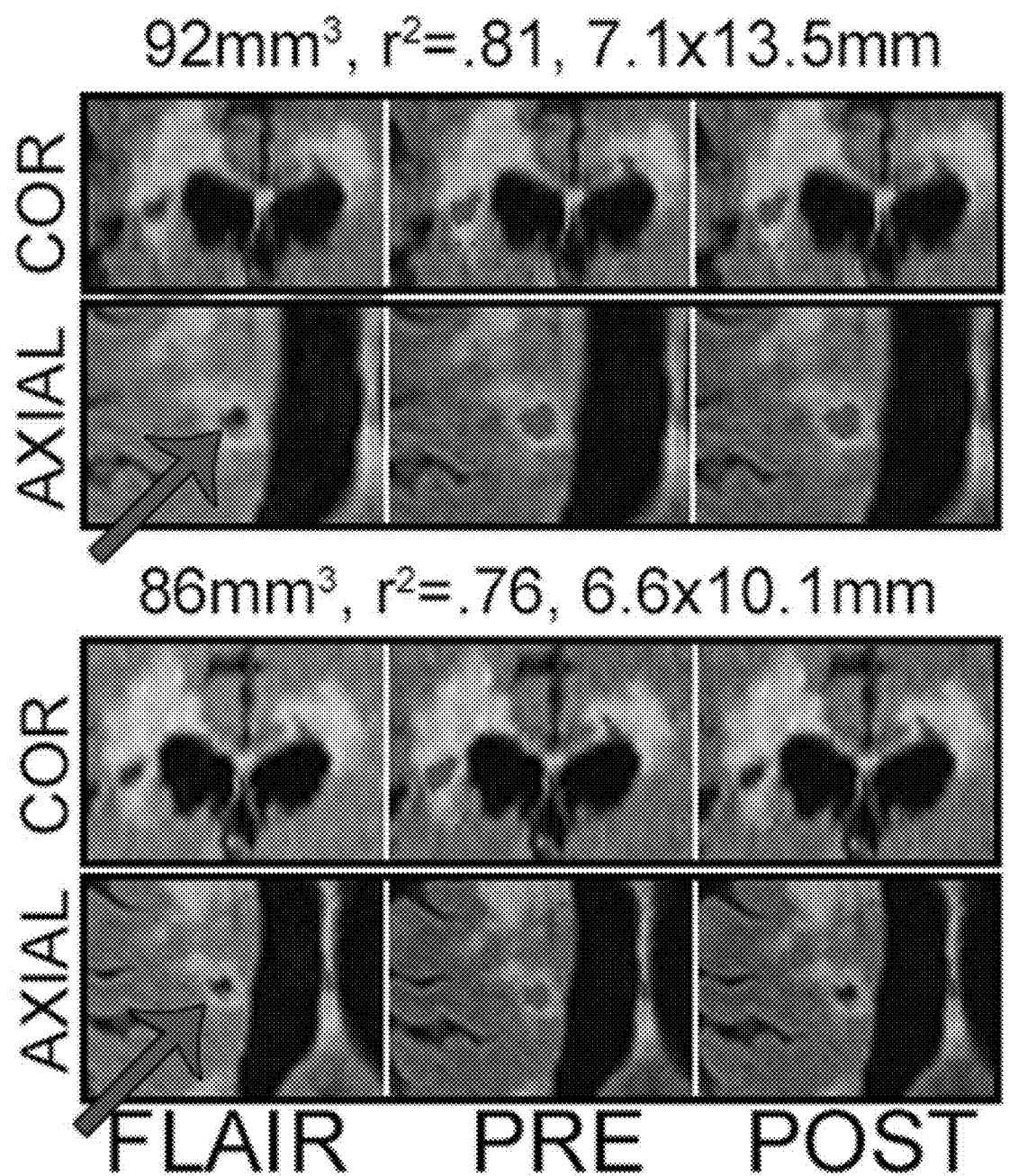
FIG. 9: An example of an unsuccessful elimination of a lacune by the morphology step (top, timepoint 1) and a successful elimination (bottom, timepoint 2) in the same subject in cohort one. Metrics shown are [volume, linearity, maximum width×length]. "pre" and "post" signify pre- and post-morphology constraint.

Finally, lacunes are difficult to differentiate from ePVS on $T_1$, and though they may often have a hyperintense rim on FLAIR, some lacunes do not. The morphological component of this automated approach serves to reduce the frequency of these types of false positives. FIG. 9 illustrates an example of the difficulty of parsing lacunes from ePVS in a single subject imaged twice; at the first scan (top), the identified object met the linearity criteria (r>0.8), while in the second scan it did not (r<0.8). Although Wardlaw et al. (LANCET NEUROL, 2013. 12(8): p. 822-38) identify lacunes by their "round or ovoid" morphology, a recent report that specifically addresses the morphology of lacunes finds that lacunes can be relatively linear and that they follow the geometry of perforating arteries. The Wardlaw report also seeks to differentiate ePVS from lacunes on the basis of their width, with PVS defined as having a diameter generally smaller than 3 mm, and lacunes having a diameter from 3 mm to 15 mm. This criterion applied in this example would have screened out the lacune (widths=7.1 and 6.6 mm on the two measurements, FIG. 9). Though a relatively small share of overall identified ePVS in this population had a width >3 mm, ePVS that have a width larger than 3 mm have an outsized relative contribution to overall burden as measured by volume, and so a width threshold of <3 mm for ePVS may lead to consequential misses. Conversely, the omission of a conservative width threshold may lead to the inclusion of outsized objects such as lacunes, as in the top row of FIG. 9. As with any automated segmentation algorithm, visual inspection of the results of this algorithm is necessary to ensure accurate segmentation of true ePVS, especially in the case of lesions that can mimic ePVS intensity and morphology. While manual inspection and removal of false alarm clusters can be time-consuming, the high positive predictive values for the algorithm (77.5% in cohort one and 87.5% in cohort two) make manual inspection manageable, as the low incidence of false alarms decreased the amount of time necessary to perform quality control.

Clinical Potential of MAPS-$T_1$:

In addition to linearity measurements, the morphological step of the disclosed algorithm provides information regarding the length and width of these structures in three dimensions at the resolution of acquisition. These particular metrics may provide additional insight into the clinical relevance of ePVS, and this tool makes these measurements readily available for large scale clinical studies that represent the power to overcome small effect sizes. For example, though the study described in this Example 2 was not powered or designed for such a comparison, it is notable that cohort two, a subject pool that was younger, more male, and had higher clinical dementia ratings than cohort one, as well as lower overall SNR, had 64% more ePVS/subject than in cohort one (50.6 vs. 82.8 ePVS/subject, FIG. 7 and FIG. 7G) after manual omission of false alarms. The accurate characterization of previously considered subpathological enlarged Virchow-Robin spaces has the potential to introduce a research path into a multitude of disease processes, and various techniques described herein can make investigations immediately available to prospective investigations that have limited imaging time available and to retrospective and/or longitudinal studies with limited datasets.

Example 3—Enlarged Perivascular Space Segmentation Using Enhanced Morphological Assessment on Single Sequence MRI Background Pathological enlargement of perivascular spaces (ePVS) has historically been considered normal, though ePVS have recently been examined more carefully in the setting of Alzheimer's (Ramirez, J., et al., J ALZHEIMERS DIS, 2015. 43(2): p. 415-24; Chen, W., et al., AJNR AM J NEURORADIOL, 2011. 32(8): p. 1490-5) and cerebrovascular disease (Charidimou, A., et al., NEUROLOGY, 2014. 82(1): p. 57-62; Roher, A. E., et al., MOL MED, 2003. 9(3-4): p. 112-22.). Example 1 describes a method to delimit ePVS using multi-contrast MRI; however, retrospective datasets may not contain four weightings, and prospective datasets may find acquisition times infeasible. In this Example 3, an ePVS segmentation method using either $T_1$ or $T_2$-weighed MRI based on morphology is demonstrated to distinguish ePVS from features of similar intensity. The single sequence MRI-based approach described here has high reliability compared to multi-sequence MRI approaches and gold standard visual ratings.

Figure 10:
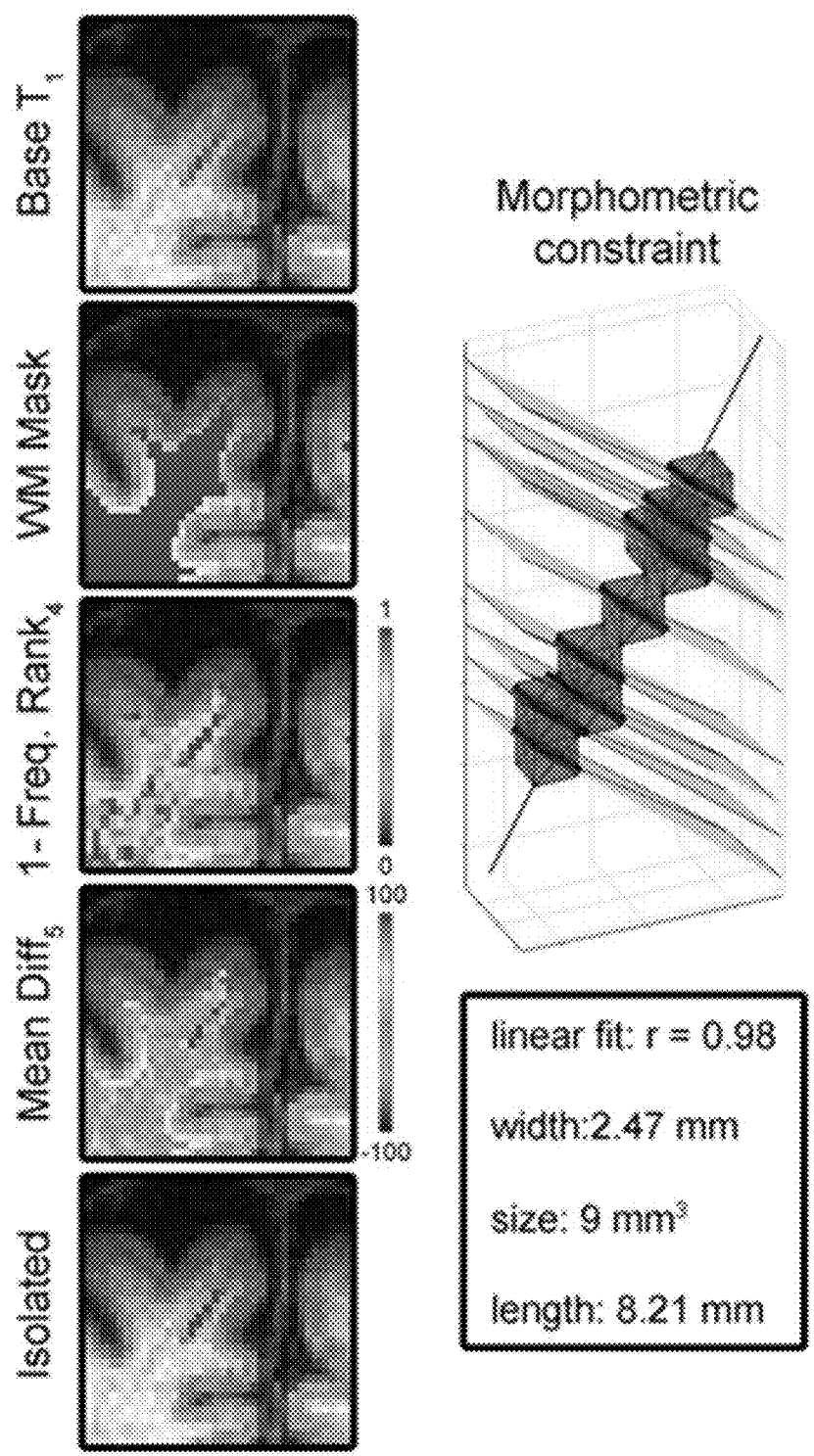
FIG. 10: Graphic representation of the disclosed method using a single sequence T1-weighted image to isolate a single ePVS in the superior frontal gyrus.

Methods $T_1$, $T_2$, PD, and FLAIR MRI were acquired in two separate sessions from fourteen subjects. The 4-sequence algorithm (mMAPS) of Example 1 was applied and three visual raters scored single slice sections. $T_1$ and $T_2$ were used for single sequence segmentation (MAPS). Inside a white matter (WM) mask, voxels were a) inverse frequency ranked ($FRANK_4$) and b) mean difference scores ($DIFF_5$) calculated (FIG. 10). For $T_1$, a voxel (with intensity i) was considered a possible ePVS if [$FRANK_4$>0.95, $DIFF_5$>0.15]. For $T_2$, [$FRANK_4$<0.95, $DIFF_5$<0.15*i]. Each ≥5 mm$^3$ cluster was further subjected to morphological filtering on linearity and width; linearity was calculated as percent explained variance of the primary eigenvector of each cluster, width was calculated as the intersection of planes normal to that vector and the edges of each cluster.

Figure 12:
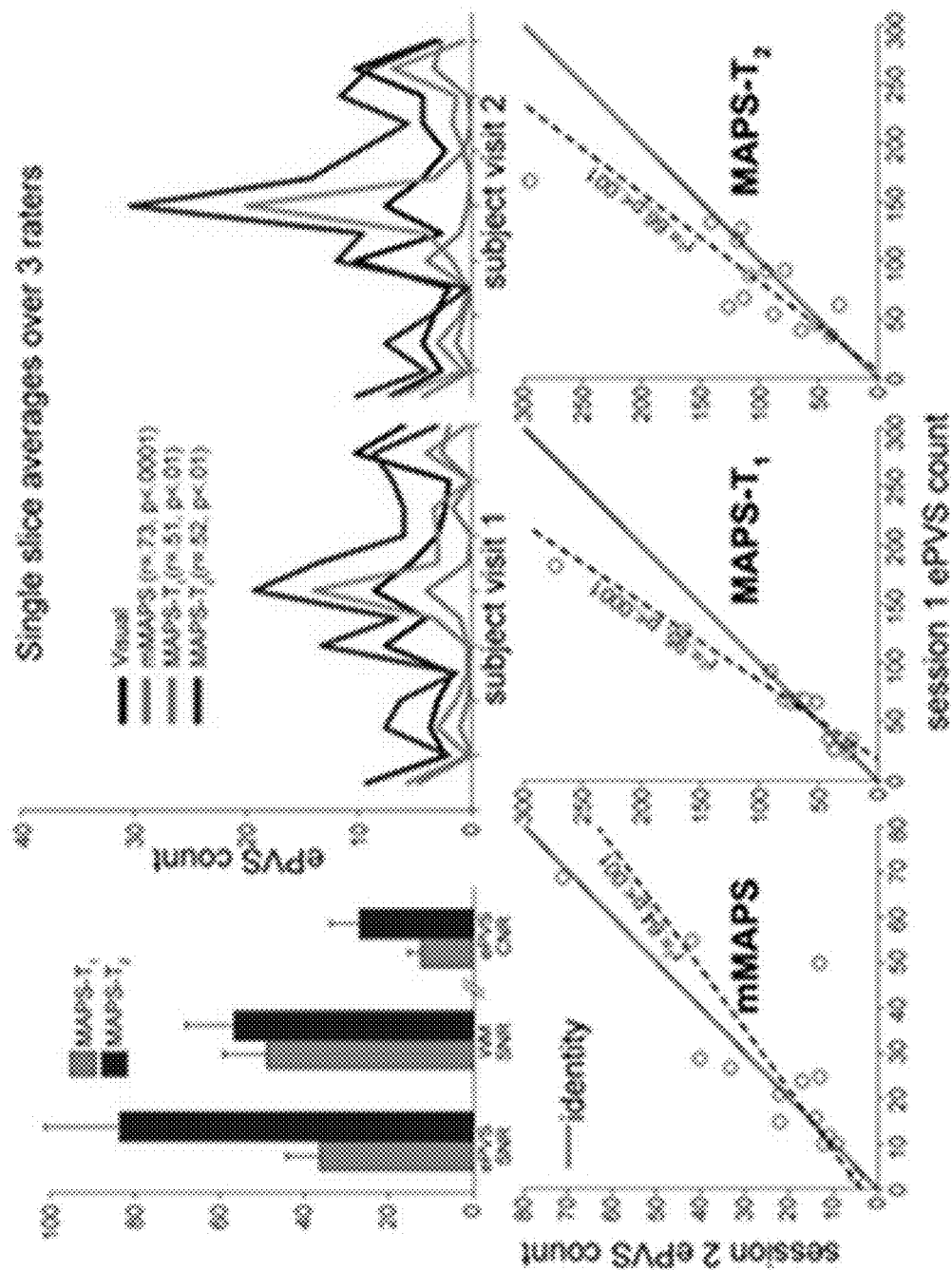
FIG. 12: A set of graphs showing results obtained using visual rating, mMAPS, MAPS-T1, and MAPS-T2 approaches. Top left: SNR and CNR measurement. Top right: method comparison of single slice averages chosen by visual raters. Bottom: within-subject correlations.

Results:

There was a high correspondence between visual ePVS counts and mMAPS, $T_1$, and $T_2$ counts over all subjects considered in Example 3; various methods in Example 3 were significantly correlated over repeated measurements in the single visually rated slice and over the whole brain (FIG. 12). SNR and CNR of segmented ePVS using single sequence methods and statistical results are available in tabular form in FIG. 11.

Discussion:

While consultation of several sequence weightings is preferred to ensure that a putative ePVS is isointense to CSF on all sequences considered in Example 3, the single sequence automated method of segmentation, based largely on refined morphological constraints, is highly correlated to expert visual counts and automated multi-sequence methods. This method may be applicable to large single sequence datasets such as ADNI, and would add valuable information regarding location and morphology of ePVS.

Example 4—MRI Image Processing System

Figure 13:
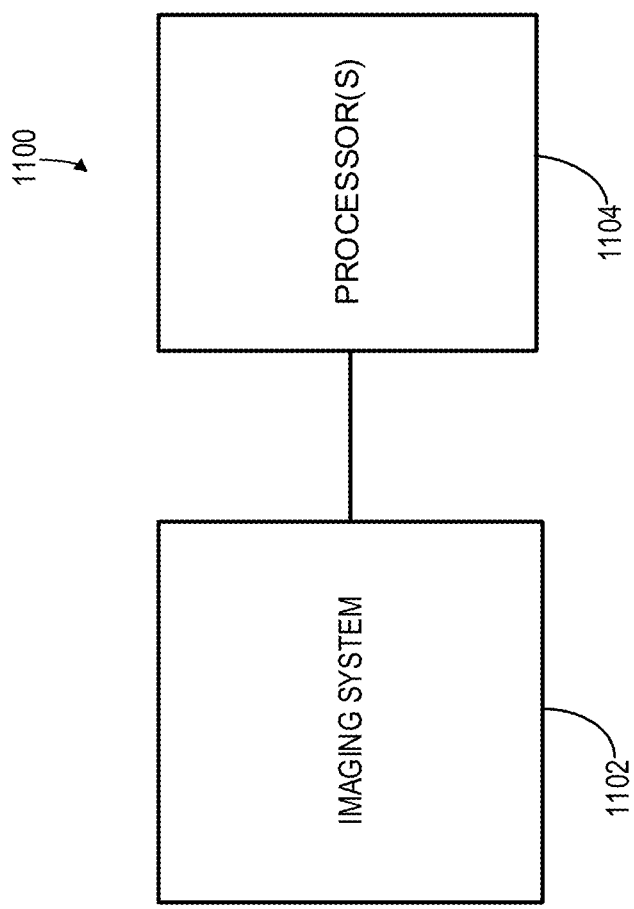
FIG. 13: A schematic showing an example system processing MRI datasets to characterize ePVS in accordance with the disclosure.

FIG. 13 schematically shows an example system 1100 for MRI image processing in accordance with various embodiments. System 1100 comprises an MRI system 1102 configured to acquire an MRI image comprising voxel intensity values and one or more processors or computing systems 1104 that are configured to implement the various processing routines described herein. MRI system 1100 can comprise an MRI system suitable clinical applications or research applications.

In various embodiments, an MRI system can be adapted to allow an operator to perform various tasks. For example, an MRI system can be adapted to allow an operator to configure and/or launch various ones of the herein described methods. In some embodiments, an MRI system can be adapted to generate, or cause to be generated, reports of various information including, for example, reports of the results of scans run on a sample.

In embodiments of MRI systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the method depicted in FIG. 1 described above, can be implemented as a computer application, computer service, computer API, computer library, and/or other computer program product.

Figure 14:
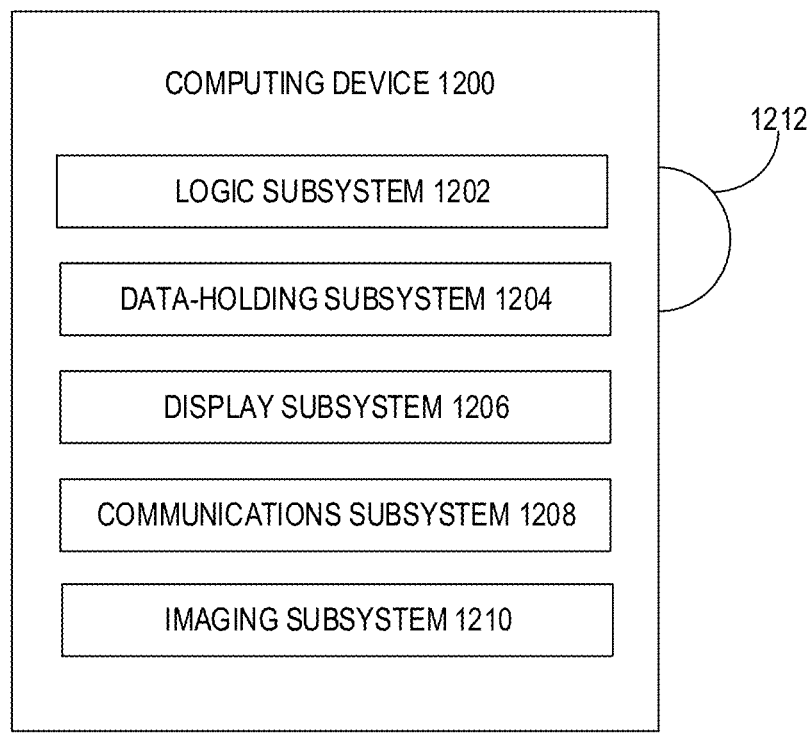
FIG. 14: A schematic showing an example of a computing system in accordance with the disclosure.

FIG. 14 schematically shows a non-limiting computing device 1200 that can perform one or more of the above described methods and processes. For example, computing device 1200 can represent a processor included in system 1100 described above, and can be operatively coupled to, in communication with, or included in an MRI system or MRI image acquisition apparatus. Computing device 1200 is shown in simplified form. It is to be understood that virtually any computer architecture can be used without departing from the scope of this disclosure. In different embodiments, computing device 1200 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1200 includes a logic subsystem 1202 and a data-holding subsystem 1204. Computing device 1200 can optionally include a display subsystem 1206, a communication subsystem 1208, an imaging subsystem 1210, and/or other components not shown in FIG. 14. Computing device 1200 can also optionally include user input devices such as manually actuated buttons, switches, keyboards, mice, game controllers, cameras, microphones, and/or touch screens, for example.

Logic subsystem 1202 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1204 can include one or more physical, non-transitory, devices configured to hold data and/or instructions executable by the logic subsystem to implement the herein described methods and processes. When such methods and processes are implemented, the state of data-holding subsystem 1204 can be transformed (e.g., to hold different data).

Data-holding subsystem 1204 can include removable media and/or built-in devices. Data-holding subsystem 1204 can include optical memory devices (e.g., CD, DVD, HD- DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1204 can include devices with one or more of the following characteristics: volatile, nonvolatile, dynamic, static, read/write, read-only, random access, sequential access, location addressable, file addressable, and content addressable. In some embodiments, logic subsystem 1202 and data-holding subsystem 1204 can be integrated into one or more common devices, such as an application specific integrated circuit or a system on a chip.

FIG. 14 also shows an aspect of the data-holding subsystem in the form of removable computer-readable storage media 1212, which can be used to store and/or transfer data and/or instructions executable to implement the herein described methods and processes. Removable computer-readable storage media 1212 can take the form of CDs, DVDs, HD-DVDs, Blu-Ray Discs, EEPROMs, flash memory cards, USB storage devices, and/or floppy disks, among others.

When included, display subsystem 1206 can be used to present a visual representation of data held by data-holding subsystem 1204. As the herein described methods and processes change the data held by the data-holding subsystem, and thus transform the state of the data-holding subsystem, the state of display subsystem 1206 can likewise be transformed to visually represent changes in the underlying data. Display subsystem 1206 can include one or more display devices utilizing virtually any type of technology. Such display devices can be combined with logic subsystem 1202 and/or data-holding subsystem 1204 in a shared enclosure, or such display devices can be peripheral display devices.

When included, communication subsystem 1208 can be configured to communicatively couple computing device 1200 with one or more other computing devices. Communication subsystem 1208 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1200 to send and/or receive messages to and/or from other devices via a network such as the Internet.

When included, imaging subsystem 1210 can be used acquire and/or process any suitable image data from various sensors or imaging devices in communication with computing device 1200. For example, imaging subsystem 1210 can be configured to acquire MRI image data, an MRI system, e.g., MRI system 1102 described above. Imaging subsystem 1210 can be combined with logic subsystem 1202 and/or data-holding subsystem 1204 in a shared enclosure, or such imaging subsystems can comprise periphery imaging devices. Data received from the imaging subsystem can be held by data-holding subsystem 1204 and/or removable computer-readable storage media 1212, for example.

Figure 15:
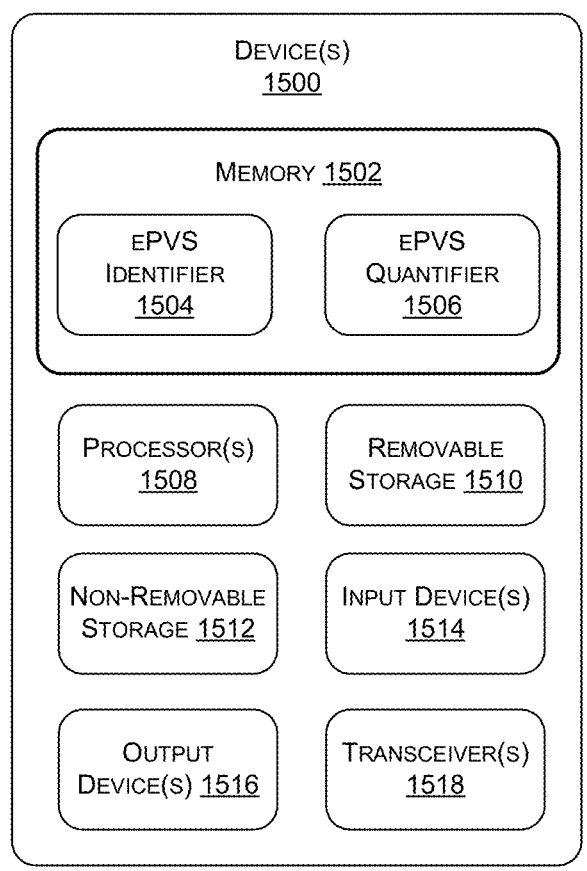
FIG. 15 illustrates examples of at least one device configured to perform any of the functionality described herein.

FIG. 15 illustrates example devices 1500 configured to intelligently allocate services to at least one reserved resource and/or at least one pooled resource in one or more delivery networks. In some embodiments, some or all of the functionality discussed in connection with FIGS. 1-14 can be implemented in the device(s) 1500. Further, the device(s) 1500 can be implemented as one or more server computers, at least one network element on a dedicated hardware, as at least one software instance running on a dedicated hardware, or as at least one virtualized function instantiated on an appropriate platform, such as a cloud infrastructure, and the like. It is to be understood in the context of this disclosure that the device(s) 1500 can be implemented as a single device or as a plurality of devices with components and data distributed among them.

As illustrated, the device(s) 1500 can include a memory 1502. In various embodiments, the memory 1502 is volatile (including a component such as Random Access Memory (RAM)), non-volatile (including a component such as Read Only Memory (ROM), flash memory, etc.) or some combination of the two.

The memory 1502 may include various components, such as an ePVS identifier 1504 and/or an ePVS quantifier 1506, consistent with various functionality described above. The ePVS identifier 1504 and/or the ePVS quantifier 1506 can comprise methods, threads, processes, applications, or any other sort of executable instructions that can be used to identify the presence of ePVS in one or more MRI datasets and/or quantify the volume of ePVS in one or more MRI datasets. The ePVS identifier 1504 and/or the ePVS quantifier 1506, as well as any of various other elements stored in the memory 1502 can also include files and databases.

The memory 1502 may include various instructions (e.g., instructions in the ePVS identifier 1504 and/or the ePVS quantifier 1506), which can be executed by at least one processor 1508 to perform operations. In some embodiments, the processor(s) 1508 includes a Central Processing Unit (CPU), a Graphics Processing Unit (GPU), or both CPU and GPU, or other processing unit or component known in the art.

The device(s) 1500 can also include additional data storage devices (removable and/or non-removable) such as, for example, magnetic disks, optical disks, or tape. Such additional storage can include removable storage 1510 and non-removable storage 1512. Tangible computer-readable media can include volatile and nonvolatile, removable and non-removable media implemented in any method or technology for storage of information, such as computer readable instructions, data structures, program modules, or other data. The memory 1502, removable storage 1510, and non-removable storage 1512 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 1502. Any such tangible computer-readable media can be part of the device(s) 1502.

The device(s) 1502 also can include input device(s) 1514, such as a keypad, a cursor control, a touch-sensitive display, voice input device, etc., and output device(s) 1516 such as a display, speakers, printers, etc. These devices are well known in the art and need not be discussed at length here. In particular implementations, a user can provide input to the device(s) 1500 via a user interface associated with the input device(s) 1514 and/or the output device(s) 1516. In various implementations, the input device(s) 1514 may include an MRI system configured to capture at least one MRI image. In some cases, the output device(s) 1516 can be controlled by the processor(s) 1508, executing instructions in the ePVS identifier 1504, to output (e.g., display) an indication that at least one MRI image contains an ePVS. In various implementations, the output device(s) 1516 can be controlled by the processor(s) 1508, executing instructions in the ePVS quantifier 1506, to output (e.g., display) an indication of a volume, width, length, and/or a cross-sectional area of an ePVS captured in at least one MRI image.

The device(s) 1500 can also include one or more wired or wireless transceiver(s) 1518. For example, the transceiver(s) 1518 can include a Network Interface Card (NIC), a network adapter, a Local Area Network (LAN) adapter, or a physical, virtual, or logical address to connect to the various base stations or networks contemplated herein, for example, or the various user devices and servers. To increase throughput when exchanging wireless data, the transceiver(s) 1518 can utilize Multiple-Input/Multiple-Output (MIMO) technology. The transceiver(s) 1518 can include any sort of wireless transceivers capable of engaging in wireless, Radio Frequency (RF) communication. The transceiver(s) 1518 can also include other wireless modems, such as a modem for engaging in Wi-Fi, WiMAX, Bluetooth, or infrared communication. In some cases, the transceiver(s) 1518 can include at least one wired transceiver configured to perform wired communication with one or more external devices.

In some implementations, the transceiver(s) 1518 can be used to communicate between various functions, components, modules, or the like, that are comprised in the device(s) 1500 and/or that are described within this document. For instance, the transceiver(s) 1518 can be used to receive MRI data from at least one MRI imaging system.

Example Clauses

The following clauses are examples of various implementations of the present disclosure:

1. A method, including: identifying at least one magnetic resonance imaging (MRI) image of a brain of a subject, the at least one MRI image including a plurality of voxels having a plurality of intensity values; identifying a set of candidate voxels based on the plurality of voxels; defining a set of candidate clusters including adjacent voxels among the set of candidate voxels; generating at least one filtered cluster by discarding one or more of the candidate clusters according to one or more morphological constraints; and determining, based on the at least one filtered cluster, whether the at least one MRI image depicts at least one enlarged perivascular space.
2. The method of clause 1, further including: causing a display device to output an indication of whether the at least one MRI image depicts the at least one enlarged perivascular space.
3. The method of clause 1 or 2, further including: receiving, from an MRI system, the at least one MRI image of the brain of the subject.
4. The method of any one of clauses 1 to 3, wherein the at least one MRI image comprises at least one of a $T_1$-weighted MRI image of the brain, a $T_2$-weighted MRI image of the brain, a fluid-attenuated inversion recovery (FLAIR) MRI image of the brain, or a proton density (PD) MRI image of the brain.
5. The method of any one of clauses 1 to 4, wherein identifying the set of candidate voxels based on the plurality of voxels includes concatenating multiple MRI images among the at least one MRI image to generate a 4D image; and identifying the set of candidate voxels based on the 4D image.
6. The method of any one of clauses 1 to 5, wherein the at least one MRI image includes a $T_1$-weighted MRI image of the brain, a $T_2$-weighted MRI image of the brain, a fluid-attenuated inversion recovery (FLAIR) MRI image of the brain, and a proton density (PD) MRI image of the brain.
7. The method of clause 6, wherein identifying the set of candidate voxels includes: generating a white matter (WM) mask by segmenting the $T_1$-weighted MRI image; identifying a first portion of the $T_1$-weighted MRI image corresponding to the WM mask; normalizing the first portion of the $T_1$-weighted MRI image by dividing each intensity value in the first portion by an average intensity value of the first portion to generate a normalized first portion; identifying a second portion of the $T_2$-weighted MRI image corresponding to the WM mask; normalizing the second portion of the $T_2$-weighted MRI image by dividing each intensity value in the second portion by an average intensity value of the second portion to generate a normalized second portion; identifying a third portion of the FLAIR MRI image corresponding to the WM mask; normalizing the third portion of the FLAIR MRI image by dividing each intensity value in the third portion by an average intensity value of the third portion to generate a normalized third portion; identifying a fourth portion of the PD MRI image corresponding to the WM mask; normalizing the fourth portion of the PD MRI image by dividing each intensity value in the fourth portion by an average intensity value of the fourth portion to generate a normalized fourth portion; concatenating the normalized first portion, the normalized second portion, the normalized third portion, and the normalized fourth portion to generate a 4D dataset; and identifying the set of candidate voxels is based on the 4D dataset.
8. The method of any one of clauses 1 to 4, wherein the at least one MRI image includes a particular MRI image, the particular MRI image being a $T_1$-weighted MRI image of the brain or a $T_2$-weighted MRI image of the brain.
9. The method of clause 8, wherein identifying the set of candidate voxels includes: segmenting the particular MRI image into a white matter (WM) mask corresponding to a set of WM voxels among the plurality of voxels; selecting a particular voxel from the set of WM voxels, the particular voxel having a particular intensity value among the plurality of intensity values
10. The method of clause 9, wherein identifying the set of candidate voxels includes calculating an inverse frequency rank (FRANK4) of the particular voxel; comparing the FRANK4 of the particular voxel to a first threshold; and identifying the particular voxel as a candidate voxel among the set of candidate voxels based on comparing the FRANK4 to the first threshold.
11. The method of clause 10, wherein the particular MRI image is a $T_1$-weighted MRI image and comparing the FRANK4 includes determining that the FRANK4 is greater than the first threshold.
12. The method of clause 10, wherein the particular MRI image is a $T_2$-weighted MRI image and comparing the FRANK 4 includes determining that the FRANK4 is less than the first threshold.
13. The method of any one of clauses 10 to 12, wherein the first threshold about 0.95.
14. The method of any one of clauses 9 to 13, wherein identifying the set of candidate voxels includes: calculating a mean difference score (DIFF5) of the particular voxel; comparing the DIFF5 of the particular voxel to a second threshold percentage of the particular intensity value; and identifying the particular voxel as a candidate voxel among the set of candidate voxels based on comparing the DIFF5 to the second threshold percentage of the particular intensity value.

15. The method of clause 14, wherein the particular MRI image is a $T_1$-weighted MRI image and comparing the DIFF5 includes determining that the DIFF5 is greater than the second threshold percentage of the particular intensity value.

16. The method of clause 14, wherein the particular MRI image is a $T_2$-weighted MRI image and comparing the DIFF5 includes determining that the DIFF5 is less than the second threshold percentage of the particular intensity value.

17. The method of any of clauses 14 to 16, wherein the threshold percentage of the particular intensity value is 15% of the particular intensity value.

18. The method of any one of clauses 1 to 17, wherein generating the at least one filtered cluster includes identifying a particular candidate cluster among the plurality of candidate clusters, the particular candidate cluster corresponding to greater than a first threshold volume.

19. The method of clause 18, wherein the first threshold volume is in a range of about 4 voxels to about 5 voxels, in a range of about 4 mm³ to about 5 mm³, or a combination thereof.

20. The method of clause 18 or 19, wherein generating the at least one filtered cluster includes identifying a linearity of the particular candidate cluster; comparing the linearity to a second threshold; and defining the particular candidate cluster as one of the at least one filtered cluster based on comparing the linearity.

21. The method of clause 20, wherein identifying the linearity includes calculating a percent explained variance of a fit longitudinal vector of the particular candidate cluster.

22. The method of clause 20 or 21 wherein identifying the linearity includes calculating a percent explained variance of a primary eigenvector of the particular cluster.

23. The method of any one of clauses 20 to 22, wherein the second threshold is about 80%.

24. The method of any one of clauses 20 to 23, wherein comparing the linearity includes determining that the linearity is greater than the second threshold.

25. The method of any one of clauses 18 to 24, wherein generating the at least one filtered cluster includes identifying a width of the particular candidate cluster; comparing the width to a third threshold; and defining the particular candidate cluster as one of the at least one filtered cluster based on comparing the width.

26. The method of clause 25, wherein identifying the width includes identifying at least one intersection of a plane normal to a primary eigenvector of the particular candidate cluster and at least one edge of the particular candidate cluster.

27. The method of clause 25 or 26, wherein the third threshold is about 15 voxels, in a range of about 15 mm to about 16 mm, or a combination thereof.

28. The method of any of clauses 1 to 27, wherein identifying the set of candidate voxels includes: identifying a particular voxel among the plurality of voxels, the particular voxel having a particular intensity value; identifying a first search field neighborhood comprising a first set of voxels among the plurality of voxels within a first radius of the particular voxel, the first set of voxels having a first set of intensity values; determining a median intensity value among the first set of intensity values; identifying a second search field neighborhood comprising a second set of voxels among the plurality of voxels within a second radius of the particular voxel, the second set of voxels having a second set of intensity values; determining differences between the particular intensity value and the second set of intensity values; determining a difference score by calculating the mean of the differences; determining that the particular intensity value is less than a first threshold percentage of the median intensity value; determining that the difference score is greater than a second threshold percentage of the particular intensity value; and identifying the particular voxel as a candidate voxel among the set of candidate voxels.

29. The method of clause 28, wherein identifying the particular voxel includes: segmenting the MRI image into a white matter (WM) mask corresponding to a set of WM voxels among the plurality of voxels; and selecting the particular voxel from the set of WM voxels.

30. The method of clause 28 or 29, wherein the first radius is shorter than the second radius.

31. The method of any one of clauses 28 to 30, wherein the first radius is about 3.5 mm and the second radius is about 5.5 mm.

32. The method of any one of clauses 1 to 31, wherein a particular candidate cluster among the candidate clusters includes greater than a threshold number of adjacent voxels.

33. The method of clause 32, wherein the particular candidate cluster includes greater than about 4 adjacent voxels or about 5 adjacent voxels.

34. The method of any one of clauses 1 to 33 wherein a first voxel that is adjacent to a second voxel includes a first corner that touches a second corner of the second voxel.

35. The method of any one of clauses 1 to 34, wherein the adjacent voxels within one candidate cluster have contiguous connectivity.

36. A system including at least one processor and memory storing instructions that, when executed by the at least one processor, cause the at least one processor to perform operations including any one of the methods of clauses 1 to 35.

37. The system of clause 36, further including an MRI system configured to capture the at least one MRI image.

38. The system of clause 36 or 37, further including an output device configured to output an indication that the at least one MRI image depicts at least one enlarged perivascular space.

39. A computer-readable medium storing non-transitory instructions executable by at least one processor to perform operations including the method of any one of clauses 1 to 35.

CONCLUSION

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The environments and individual elements described herein may of course include many other logical, programmatic, and physical components, of which those shown in the accompanying figures are merely examples that are related to the discussion herein.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

As will be understood by one of ordinary skill in the art, each embodiment disclosed herein can comprise, consist essentially of, or consist of its particular stated element(s), step(s), ingredient(s), and/or component(s). Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiments.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing various implementations of the disclosure on (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure, and does not pose a limitation on the scope of the disclosure and/or the scope of the claims. No language in the specification should be construed as indicating any non-claimed element essential to the practice of the claimed invention.

Groupings of alternative elements or embodiments of the claimed invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of the claimed invention are described herein, including the best mode known to the inventors. Of course, variations on these described embodiments will become apparent to those of ordinary skill in the art upon reading the foregoing description. The inventors expect skilled artisans to employ such variations as appropriate, and the inventors intend for the claimed invention to be practiced otherwise than specifically described herein. Accordingly, the claimed invention includes all modifications and equivalents of the subject matter recited in the claims appended hereto as permitted by applicable law. Moreover, any combination of the above-described elements in all possible variations thereof is encompassed by the claimed invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments disclosed herein are illustrative of at least some principles of the claims. Other modifications that may be employed are within the scope of the disclosure. Thus, by way of example, but not of limitation, alternative configurations of various disclosed implementations may be utilized in accordance with the teachings herein. Accordingly, the claimed invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Explicit definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A system, comprising
   a Magnetic Resonance Imaging (MRI) system;
   an output device;
   at least one processor; and
   memory storing instructions that, when executed by the at least one processor, cause the at least one processor to perform operations that comprise:
   receiving, from the MRI system, an MRI image of a brain of a subject, the MRI image being a $T_1$-weighted MRI image comprising a plurality of voxels having a plurality of intensity values;
   identifying a set of candidate voxels among the plurality of voxels based on the plurality of intensity values;
   defining a set of candidate clusters comprising adjacent voxels among the set of candidate voxels;
   generating at least one filtered cluster by discarding one or more of the candidate clusters according to one or more morphological constraints; and
   causing the output device to output an indication that the at least one filtered cluster corresponds to at least one enlarged perivascular space.

2. The system of claim 1, wherein identifying the set of candidate voxels comprises:
   identifying a particular voxel among the plurality of voxels, the particular voxel having a particular intensity value;
   identifying a first search field neighborhood comprising a first set of voxels among the plurality of voxels within a first radius of the particular voxel, the first set of voxels having a first set of intensity values;
   determining a median intensity value among the first set of intensity values;
   identifying a second search field neighborhood comprising a second set of voxels among the plurality of voxels within a second radius of the particular voxel, the second set of voxels having a second set of intensity values;
   determining differences between the particular intensity value and the second set of intensity values;
   determining a difference score by calculating the mean of the differences;
   determining that the particular intensity value is less than a first threshold percentage of the median intensity value;
   determining that the difference score is greater than a second threshold percentage of the particular intensity value; and
   identifying the particular voxel as a candidate voxel among the set of candidate voxels.

3. The system of claim 2, wherein identifying the particular voxel comprises:
   segmenting the MRI image into a white matter (WM) mask corresponding to a set of WM voxels among the plurality of voxels; and
   selecting the particular voxel from the set of WM voxels.

4. The system of claim 1, wherein identifying the set of candidate voxels comprises:
   segmenting the MRI image into a white matter (WM) mask corresponding to a set of WM voxels among the plurality of voxels;
   selecting a particular voxel from the set of WM voxels, the particular voxel having a particular intensity value among the plurality of intensity values;
   calculating an inverse frequency rank (FRANK4) of the particular voxel;
   calculating a mean difference score (DIFF5) of the particular voxel;
   determining that the FRANK4 of the particular voxel is greater than a first threshold;
   determining that the DIFF5 of the particular voxel is greater than a second threshold percentage of the particular intensity value; and
   identifying the particular voxel as a candidate voxel among the set of candidate voxels.

5. The system of claim 1, wherein generating the at least one filtered cluster comprises:
   identifying a particular candidate cluster among the plurality of candidate clusters, the particular candidate cluster comprising greater than a first threshold number of voxels;
   identifying a linearity of the particular candidate cluster by calculating a percent explained variance of a fit longitudinal vector of the particular candidate cluster;
   identifying a width of the particular candidate cluster;
   determining that the linearity of the particular candidate cluster is greater than a second percentage threshold;
   determining that the width of the particular candidate cluster is less than a width of a third threshold number of voxels; and
   defining the particular candidate cluster as one of the at least one filtered cluster.

6. The system of claim 1, wherein generating the at least one filtered cluster comprises:
   identifying a particular candidate cluster among the plurality of candidate clusters, the particular candidate cluster corresponding to greater than a first threshold volume;
   identifying a linearity of the particular candidate cluster by calculating a percent explained variance of a primary eigenvector of the particular cluster;
   identifying a width of the particular candidate cluster by identifying at least one intersection of a plane normal to the primary eigenvector and at least one edge of the particular candidate cluster;

determining that the linearity of the particular candidate cluster is greater than a second threshold;

determining that the width of the particular candidate cluster is less than a third threshold; and defining the particular candidate cluster as one of the at least one filtered cluster.

7. A system, comprising:

at least one processor; and memory storing instructions that, when executed by the at least one processor, cause the at least one processor to perform operations that comprise:

identifying at least one magnetic resonance imaging (MRI) image of a brain of a subject, the at least one MRI image comprising a plurality of voxels having a plurality of intensity values;

identifying a set of candidate voxels based on the plurality of voxels;

defining a set of candidate clusters comprising adjacent voxels among the set of candidate voxels;

generating at least one filtered cluster by discarding one or more of the candidate clusters according to one or more morphological constraints; and determining, based on the at least one filtered cluster, that the at least one MRI image depicts at least one enlarged perivascular space.

8. The system of claim 7, wherein the at least one MRI image comprises a $T_1$-weighted MRI image of the brain, a $T_2$-weighted MRI image of the brain, a fluid-attenuated inversion recovery (FLAIR) MRI image of the brain, and a proton density (PD) MRI image of the brain, and wherein identifying the set of candidate voxels comprises:

generating a white matter (WM) mask by segmenting the $T_1$-weighted MRI image;

identifying a first portion of the $T_1$-weighted MRI image corresponding to the WM mask;

normalizing the first portion of the $T_1$-weighted MRI image by dividing each intensity value in the first portion by an average intensity value of the first portion to generate a normalized first portion;

identifying a second portion of the $T_2$-weighted MRI image corresponding to the WM mask;

normalizing the second portion of the $T_2$-weighted MRI image by dividing each intensity value in the second portion by an average intensity value of the second portion to generate a normalized second portion;

identifying a third portion of the FLAIR MRI image corresponding to the WM mask;

normalizing the third portion of the FLAIR MRI image by dividing each intensity value in the third portion by an average intensity value of the third portion to generate a normalized third portion;

identifying a fourth portion of the PD MRI image corresponding to the WM mask;

normalizing the fourth portion of the PD MRI image by dividing each intensity value in the fourth portion by an average intensity value of the fourth portion to generate a normalized fourth portion;

concatenating the normalized first portion, the normalized second portion, the normalized third portion, and the normalized fourth portion to generate a 4D dataset; and identifying the set of candidate voxels is based on the 4D dataset.

9. The system of claim 7, wherein the at least one MRI image comprises a particular MRI image that comprises the plurality of voxels, the particular MRI image being a $T_1$-weighted MRI image or a $T_2$-weighted MRI image, and wherein identifying the set of candidate voxels comprises:

segmenting the particular MRI image into a white matter (WM) mask corresponding to a set of WM voxels among the plurality of voxels;

selecting a particular voxel from the set of WM voxels, the particular voxel having a particular intensity value among the plurality of intensity values;

calculating an inverse frequency rank (FRANK4) of the particular voxel;

calculating a mean difference score (DIFF5) of the particular voxel;

comparing the FRANK4 of the particular voxel to a first threshold;

comparing the DIFF5 of the particular voxel to a second threshold percentage of the particular intensity value; and identifying the particular voxel as a candidate voxel among the set of candidate voxels based on comparing the FRANK4 to the first threshold and comparing the DIFF5 to the second threshold percentage of the particular intensity value.

10. The system of claim 7, wherein the at least one MRI image comprises a particular MRI image that comprises the plurality of voxels, the particular MRI image being a $T_1$-weighted MRI image or a $T_2$-weighted MRI image, and wherein generating the at least one filtered cluster comprises:

identifying a particular candidate cluster among the plurality of candidate clusters, the particular candidate cluster corresponding to greater than a first threshold volume;

identifying a linearity of the particular candidate cluster by calculating a percent explained variance of a primary eigenvector of the particular cluster;

identifying a width of the particular candidate cluster by identifying at least one intersection of a plane normal to the primary eigenvector and at least one edge of the particular candidate cluster;

comparing the linearity of the particular candidate cluster to a second threshold;

comparing the width of the particular candidate cluster to a third threshold; and defining the particular candidate cluster as one of the at least one filtered cluster based on comparing the linearity to the second threshold and comparing the width to the third threshold.

11. A method for identifying perivascular spaces, the method comprising:

receiving a magnetic resonance imaging (MRI) dataset comprised of voxels having a plurality of intensity values;

identifying a set of candidate voxels within the MRI dataset based on the plurality of intensity values;

grouping the set of candidate voxels into a set of first clusters;

filtering the set of first clusters to generate a set of second clusters;

filtering the set of second clusters based on a morphologic constraint, thereby identifying an enlarged perivascular space in the MRI dataset.

12. The method of claim 11, further comprising:

calculating a volume of the enlarged perivascular space in the MRI dataset; and causing an output device to output an indication of the volume of the enlarged perivascular space.

13. The method of claim 11, wherein identifying the set of candidate voxels comprises applying a local intensity variability model to the MRI dataset.

14. The method of claim 11, wherein grouping the set of candidate voxels comprises identifying sets of voxels having contiguous connectivity, wherein a first voxel and a second voxel having contiguous connectivity share at least one vertex.

15. The method of claim 11, wherein filtering the set of first clusters to generate the set of second clusters comprises selecting the second clusters from the set of first clusters, each one of the second clusters having a total voxel volume that is greater than a volume threshold.

16. The method of claim 15, wherein the volume threshold corresponds to a volume in a range of 4 mm$^3$ to 5 mm$^3$.

17. The method of claim 11, wherein filtering the set of second clusters based on the morphological constraint comprises:
    calculating a metric of linearity of each of the second clusters to generate a set of linearities; and
    identifying the enlarged perivascular space based on one or more of the second clusters that each correspond to a linearity that is greater than a prescribed linearity threshold.

18. The method of claim 17, wherein the metric of linearity of a particular cluster among the second clusters is calculated as the percent explained variance of the primary eigenvector of the particular cluster.

19. The method of claim 11, further comprising:
    calculating a metric of width of each of the second clusters to generate a set of widths; and
    identifying the enlarged perivascular space based on one or more of the second clusters that each correspond to a width that is less than or equal to a prescribed width threshold.

20. The method of claim 19, wherein calculating the metric of width for each of the second clusters comprises:
    calculating a primary eigenvector of each of the second clusters to generate a set of eigenvectors; and
    calculating a particular metric of width among the set of widths by identifying an intersection of planes normal to a particular primary eigenvector of a particular second cluster and one or more edges of the particular second cluster.

* * * * *